US006627767B2

(12) United States Patent
Liu et al.

(10) Patent No.: US 6,627,767 B2
(45) Date of Patent: Sep. 30, 2003

(54) AMINO(OXO) ACETIC ACID PROTEIN TYROSINE PHOSPHATASE INHIBITORS

(75) Inventors: Gang Liu, Gurnee, IL (US); Yihong Li, Carmel, IN (US); David A. Janowick, Beach Park, IL (US); Zhonghua Pei, Libertyville, IL (US)

(73) Assignee: Abbott Laboratories, Abott Park, IL (US)

( * ) Notice: Subject to any disclaimer, the term of this patent is extended or adjusted under 35 U.S.C. 154(b) by 0 days.

(21) Appl. No.: 09/934,765

(22) Filed: Aug. 22, 2001

(65) Prior Publication Data

US 2002/0035136 A1 Mar. 21, 2002

Related U.S. Application Data

(60) Provisional application No. 60/228,656, filed on Aug. 29, 2000.

(51) Int. Cl.$^7$ ............................................ C07C 229/00
(52) U.S. Cl. .......................... 560/19; 560/37; 562/433; 562/442
(58) Field of Search ................................ 560/8, 19, 21, 560/22, 23, 30, 37; 562/400, 405, 433, 441, 442

(56) References Cited

U.S. PATENT DOCUMENTS

| | | | |
|---|---|---|---|
| 3,836,541 A | | 9/1974 | Johnson, et al. |
| 5,192,358 A | * | 3/1993 | Rentzea et al. ............. 504/307 |
| 5,532,267 A | | 7/1996 | Nakayama et al. |

FOREIGN PATENT DOCUMENTS

| | | |
|---|---|---|
| WO | 9315044 | 8/1993 |
| WO | 9945267 | 9/1999 |
| WO | 9946236 | 9/1999 |
| WO | 9946237 | 9/1999 |
| WO | 9946267 | 9/1999 |
| WO | 9946268 | 9/1999 |

OTHER PUBLICATIONS

CA:96:195712 abs of S Afr J Sci by Vermeulen et al 77(12) pp 566–9 1981.*
CA:83:172416 abs of J Med Chem by Sellstedt et a 18(9) pp 926–33 1975I.*
CA:69:106477 abs of Yakugaku Zasshi by Kametani et al 88(4) pp 445–52 1968.*
CA:112: 76634 abs of JP01226861 Sep. 11, 1989.*
CA:125:33249 abs of Synthesis by Henneuse et al (4) pp 495–501 1996.*
CA:123:284861 abs of Journal of Organic Chem by Minisci et al 60(17) pp 5430–3 1995.*
CA:128:88636 abs of Molecules [Electronic publications] by Lin, Shu Kun 2(4) M4 1997.*
CA 112:98405 abs of EP 330469 Aug. 1989.*
Fischer, et al., "Protein Tyrosine Phosphatases: A Diverse Family of Intracellular and Transmembrane Enzymes", *Science*, 253:401–406 (1991).
Flint, et al., "Multi–site phosphorylation of the protin tyrosine phosphatase, PTP1B: identification of cell cycle regulated and phorbol ester stimulated sites of phosphorylation", *The EMBO Journ.*, 12(5):1937–1946 (1993).
T. Hunter & J.A. Cooper, "Protein–Tyrosine Kinases", *Ann. Rev. Biochem.*, 54:897–930 (1985).
Mauro, et al., "Identification of a Hormonally Regulated Protein Tyrosine Phosphatase Associated with Bone and Testicular Differentiation", *The Journ. Of Biol. Chem.*, 269(48):30659–30667 (1994).
Noguchi, et al., "role of SH–PTP2, a Protein–Tyrosine Phosphatase with Src Homology 2 Domains, in Insulin–Stimulated Ras Activation", *Molecular and Cellular Biology*, 14(10):6674–6682 (1994).
Wang, et al., "Mechanism of Inhibition of Protein–Tyrosine Phosphatases by Disodium Aurothiomalate", *Biochemical Pharmacology*, 54:703–711 (1997).
Wiener, et al., "Over expressionof the Protein Tyrosine Phosphatase PTP1B in Human Breast Cancer: Association with p185 Protein Expression", *Journ. Of the Nat. Cancer Inst.*, 86(5):372–378 (1994).
Rault, et., *Heterocycles*, 38(4):911–818 (1994) Database accession No. 7044775.
Godefroi, et al., *Journ. or Organic Chem.*, 32:1259 (1967) Database accession No. 2732230.
Godfroi, et al., *Journ. of Organic Chem.*, 32:1259 (1967) Database accession No. 2732219.
Klaubert, et al., *Journ. of Medicinal Chem.*, 24(6):748–752 (1981) Database accession No. 5045520.

* cited by examiner

*Primary Examiner*—Jean F. Vollano
(74) *Attorney, Agent, or Firm*—Christopher P. Rogers

(57) ABSTRACT

(I)

$$R^4 \underset{A}{\overset{(R^3)_d}{\underset{\|}{\overline{\phantom{XX}}}}} \overset{B}{\underset{L^2}{\overline{\phantom{XX}}}} L^1 \underset{R^2}{\overset{O}{\underset{\|}{N}}} \overset{O}{\underset{\|}{\overline{\phantom{XX}}}} O \cdot R^1,$$

or therapeutically acceptable salts thereof, are protein tyrosine kinase PTP1B inhibitors. Preparation of the compounds, compositions containing the compounds, and treatment of diseases using the compounds are disclosed.

24 Claims, No Drawings

AMINO(OXO) ACETIC ACID PROTEIN TYROSINE PHOSPHATASE INHIBITORS

This application claims priority to the provisional application Ser. No. 60/228,656 filed on Aug. 29, 2000.

TECHNICAL FIELD

The instant invention is directed to compounds useful for inhibiting protein tyrosine phosphatase PTP1B, preparation of the compounds, compositions containing the compounds, and treatment of diseases using the compounds.

BACKGROUND OF THE INVENTION

PTP1B belongs to a family of protein tyrosine phosphatases involved in the regulation of the cellular signalling mechanisms which are involved in metabolism, growth, proliferation and differentiation (*Science* 253:401–6 (1991)). Overexpression or altered activity of tyrosine phosphatase PTP1B can also contribute to the progression of various diseases (*Ann. Rev. Biochem.*, 54:897–930 (1985)); and there is evidence which suggests inhibition of protein tyrosine phosphatase PTP1B is therapeutically beneficial for the treatment of diseases such as type I and II diabetes, obesity, autoimmune disease, acute and chronic inflammation, osteoporosis and various forms of cancer (*J. Natl. Cancer Inst.* 86:372–8 (1994); *Mol. Cell. Biol.* 14:6674–6682 (1994); *The EMBO J.* 12:1937–46 (1993); *J. Biol. Chem.* 269:30659–30667 (1994); and Biochemical Pharmacology 54:703–711 (1997)).

Because of the important role played by unregulated protein tyrosine phosphatase PTP1B in these diseases, agents which inhibit the enzyme have been the subject of active current research for their clinical potential. Reference is made to WO 99/46236, WO 99/46237, WO 99/46267 and WO 99/46268; and although each teaches certain heteroaryl and heterocycle amino(oxo)acetic acid protein tyrosine phosphatase PTP1B inhibitors, there is still a need for protein tyrosine phosphatase PTP1B inhibitors with modified or improved profiles of activity.

SUMMARY OF THE INVENTION

In the principle embodiment of the instant invention, therefore, are provided protein tyrosine phosphatase PTP1B inhibitors of formula (I):

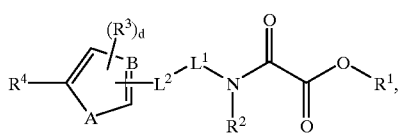

(I)

or therapeutically acceptable salts thereof, wherein

A is selected from N(H), O, S, N=C(H), and C(H)=C(H);

B is selected from N and C(H);

with the proviso that when A is N=C(H) or C(H)=C(H), B is C(H);

d is 0, 1, or 2;

$L^1$ is a covalent bond or O;

$L^2$ is selected from CH($R^6$) and CH$_2$CH($R^6$);

$R^1$ is selected from hydrogen and a carboxy protecting group;

$R^2$ is selected from hydrogen, aminoalkyl, loweralkyl, cycloalkyl, cycloalkylalkyl, cycloalkenyl, cycloalkenylalkyl, aryl, heteroaryl, heterocycle, arylalkyl, heteroarylalkyl, (heterocycle)alkyl, hydroxyalkyl, and haloalkyl;

each $R^3$ is independently selected from hydrogen, loweralkoxy, alkoxyalkyl, alkoxyalkenyl, alkoxyalkoxy, alkoxycarbonyl, alkoxycarbonylalkyl, alkoxycarbonylalkenyl, alkoxycarbonylalkoxy, aryl, arylalkyl, arylalkenyl, arylalkoxy, carboxamido, carboxamidoalkyl, carboxamidoalkenyl, carboxamidoalkoxy, carboxy, carboxyalkyl, carboxyalkenyl, carboxyalkoxy, halo, heteroaryl, heteroarylalkyl, heteroarylalkenyl, and heteroarylalkoxy; or A is C(H)=C(H), and two of $R^3$ are on adjacent atoms and, taken together with the atoms to which they are attached, are phenyl, wherein the phenyl can be optionally substituted with one or two substituents independently selected from loweralkoxy, alkoxycarbonylalkenyl, alkoxycarbonylalkoxy, aryl, carboxamidoalkenyl, carboxamidoalkoxy, carboxyalkenyl, carboxyalkoxy, halo, and heteroarylalkoxy;

with the proviso that $R^3$ is connected to a substitutable carbon atom;

$R^4$ is selected from hydrogen, alkoxy, alkoxycarbonylalkyl, alkoxycarbonylalkenyl, aryl, arylalkyl, arylalkoxy, arylthioxyalkyl, carboxamidoalkenyl, carboxamidoalkyl, carboxyalkyl, carboxylalkenyl, heteroaryl, heteroarylalkyl, heteroarylalkoxy, heteroarylthioxyalkyl, halo, and $R^7$-T-;

with the proviso that at when $R^4$ is hydrogen, at least one of $R^3$ is other than hydrogen;

$R^6$ is selected from hydrogen, aryl, arylalkyl, heteroaryl, heteroarylalkyl, cycloalkyl, cycloalkylalkyl, cycloalkenyl, cycloalkenylalkyl, heterocycle, and (heterocycle)alkyl;

$R^7$ is selected from aryl and heteroaryl;

T is selected from C(O)N($R^8$), N($R^8$)C(O), N($R^8$), OC(O)N($R^8$), N($R^8$)C(O)O, C(O), OC(O), (O)CO, O, S, S(O), SO$_2$, C(O), OC(O)O, N($R^8$)C(O)N($R^8$), and C(O)OC(O);

wherein the asymmetric groups defining T are drawn with their left ends attached to $R^7$ and their right ends attached to the ring and; and $R^8$ is selected from hydrogen and loweralkyl.

In another embodiment of the instant invention are provided compounds of formula (II)

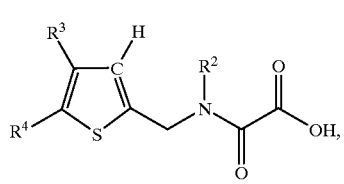

(II)

or therapeutically acceptable salts thereof, wherein $R^2$ and $R^4$ are defined previously, and $R^3$ is selected from hydrogen and halo.

In a preferred embodiment of the compounds of formula (II), $R^2$ is arylalkyl, and $R^4$ is aryl.

In still another embodiment of the instant invention are provided compounds of formula (III)

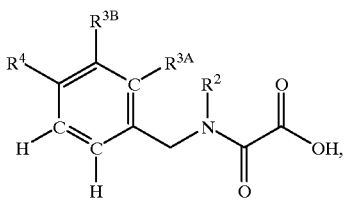

(III)

or therapeutically acceptable salts thereof, wherein $R^2$ and $R^4$ are defined previously; $R^{3A}$ is selected from hydrogen, loweralkoxy, alkoxycarbonylalkenyl, alkoxycarbonylalkoxy, aryl, carboxamidoalkenyl, carboxamidoalkoxy, carboxyalkenyl, carboxyalkoxy, halo, and heteroarylalkoxy; and $R^{3B}$ is selected from hydrogen and halo.

In a preferred embodiment of the compounds of formula (III), $R^2$ is hydrogen, arylalkyl, cycloalkyl, or (heterocycle)alkyl; and $R^4$ is aryl or heteroarylalkoxy.

In still another embodiment of the instant invention are provided compounds of formula (IV)

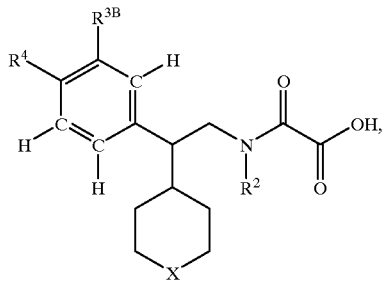

(IV)

or therapeutically acceptable salts thereof, wherein $R^2$ and $R^4$ are defined previously; $R^{3b}$ is selected from hydrogen and aryl; X is selected from $CH_2$ and $N(R^X)$; and $R^X$ is selected from alkanoyl, alkylsulfonyl, arylsulfonyl, aryloyl, arylsulfonyl, carboxamidoalkyl, and (heterocycle)alkyl.

In a preferred embodiment of the compounds of formula (IV), $R^2$ is hydrogen, arylalkyl, arylalkyl, (heterocycle)alkyl, or aminoalkyl; and $R^4$ is hydrogen, halo, aryl, alkoxycarbonylalkenyl, carboxyalkenyl, heteroaryl, or carboxamidoalkenyl.

In still another embodiment of the instant invention are provided compounds of formula (V)

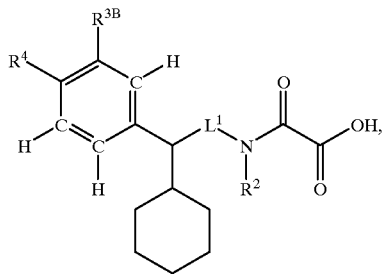

(V)

or therapeutically acceptable salts thereof, wherein $L^1$, $R^2$, and $R^4$ are defined previously; and $R^{3b}$ selected from hydrogen and heteroaryl.

In a preferred embodiment of the compounds of formula (V), $L^1$ is a covalent bond or O; $R^2$ is hydrogen; and $R^4$ is hydrogen, halo, aryl, or heteroarylalkoxy.

In still another embodiment of the instant invention are provided compounds of formula (VI)

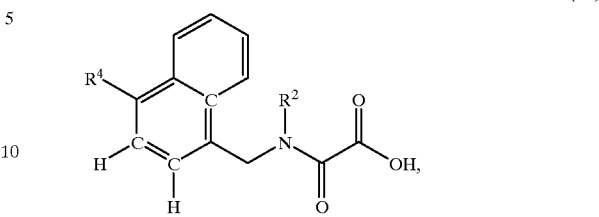

(VI)

or therapeutically acceptable salts thereof, wherein $R^2$ and $R^4$ are defined previously.

In a preferred embodiment of the compounds of formula (VI), $R^2$ is hydroxyalkyl or arylalkyl and $R^4$ is loweralkoxy, alkoxy, or aryl.

In still another embodiment of the instant invention are provided a method for preparing the compounds of formula (I),
the method comprising:
(a) reacting a compound of formula (Ia)

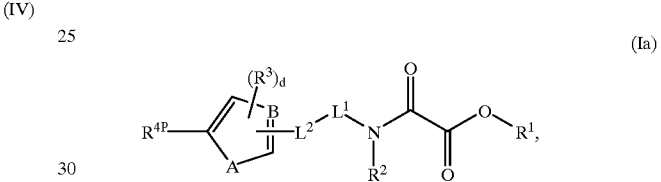

(Ia)

or therapeutically acceptable salts thereof,
wherein
A, B, d, $L^1$, $L^2$, $R^1$, and $R^2$ are defined previously; and
$R^{4P}$ is coupling promoter group selected from the group consisting of chloride, bromide, trifluoromethanesulfonate, iodide, and hydroxy,
with a coupling partner, a base, and, optionally, a palladium catalyst; and
(b) optionally hydrolyzing the product of step (a).

In a preferred embodiment of the method, the coupling partner is selected from a substituted alkene, an optionally substituted arylboronic acid, an optionally substituted heteroarylboronic acid, an optionally substituted aryl trialkylstannane, an optionally substituted heteroaryl trialkylstannane, and an optionally substituted alkyl halide; and the palladium catalyst is selected from tetrakistriphenylphosphinepalladium(O), palladium(II) bis(triphenylphosphine)dichloride, and dipalladium tris(dibenzylidineacetone).

In still another embodiment of the instant invention is provided a method for inhibiting protein tyrosine phosphatase comprising administering a therapeutically effective amount of a compound of formula (I).

In still another embodiment of the instant invention is provided a method for inhibiting protein tyrosine phosphatase comprising administering a therapeutically effective amount of a compound of formula (II).

In still another embodiment of the instant invention is provided a method for inhibiting protein tyrosine phosphatase comprising administering a therapeutically effective amount of a compound of formula (III).

In still another embodiment of the instant invention is provided a method for inhibiting protein tyrosine phosphatase comprising administering a therapeutically effective amount of a compound of formula (IV).

In still another embodiment of the instant invention is provided a method for inhibiting protein tyrosine phosphatase comprising administering a therapeutically effective amount of a compound of formula (V).

In still another embodiment of the instant invention is provided a method for inhibiting protein tyrosine phosphatase comprising administering a therapeutically effective amount of a compound of formula (VI).

In still another embodiment of the instant invention is provided a method for treating diseases in a patient in recognized need of such treatment comprising administering to the patient a therapeutically effective amount of a compound of formula (I).

In still another embodiment of the instant invention is provided a method for treating diseases in a patient in recognized need of such treatment comprising administering to the patient a therapeutically effective amount of a compound of formula (II).

In still another embodiment of the instant invention is provided a method for treating diseases in a patient in recognized need of such treatment comprising administering to the patient a therapeutically effective amount of a compound of formula (III).

In still another embodiment of the instant invention is provided a method for treating diseases in a patient in recognized need of such treatment comprising administering to the patient a therapeutically effective amount of a compound of formula (IV).

In still another embodiment of the instant invention is provided a method for treating diseases in a patient in recognized need of such treatment comprising administering to the patient a therapeutically effective amount of a compound of formula (V).

In still another embodiment of the instant invention is provided a method for treating diseases in a patient in recognized need of such treatment comprising administering to the patient a therapeutically effective amount of a compound of formula (VI).

In still another embodiment of the instant invention is provided a composition comprising a compound of formula (I) in combination with a therapeutically acceptable excipient.

In still another embodiment of the instant invention is provided a composition comprising a compound of formula (II) in combination with a therapeutically acceptable excipient.

In still another embodiment of the instant invention is provided a composition comprising a compound of formula (III) in combination with a therapeutically acceptable excipient.

In still another embodiment of the instant invention is provided a composition comprising a compound of formula (IV) in combination with a therapeutically acceptable excipient.

In still another embodiment of the instant invention is provided a composition comprising a compound of formula (V) in combination with a therapeutically acceptable excipient.

In still another embodiment of the instant invention is provided a composition comprising a compound of formula (VI) in combination with a therapeutically acceptable excipient.

DETAILED DESCRIPTION OF THE INVENTION

The instant invention provides a series of compounds which inhibit protein tyrosine phosphatase PTP1B. The compounds comprise a proximal, optionally substituted aryl or heteroaryl ring tethered through an optionally substituted linker to the nitrogen of an amino(oxo)acetic acid group. The proximal ring is optionally substituted phenyl, naphthyl, furanyl, thienyl, pyrrolyl, pyridyl, oxazolyl, or thiazolyl and has attached thereto at least one distal substituent other than hydrogen. The linker group connecting the proximal ring to the amino(oxo)acetic acid group is optionally substituted methylene or ethylene which can be optionally interrupted at the carbon-nitrogen juncture by an oxygen atom. When present, the preferred substituents on the linker group are cycloalkyl, especially cyclohexyl, and heterocycle, preferably optionally N-substituted piperidiny-4-yl.

As used throughout the specification of the instant invention, the following terms, as used herein, have the meanings indicated:

The term "alkanoyl," refers to a loweralkyl group attached to the parent molecular group through a carbonyl.

The term "alkanoyloxy," refers to an alkanoyl group attached to the parent molecular group through an oxygen atom.

The term "alkoxy," refers to an alkyl group attached to the parent molecular group through an oxygen atom.

The term "alkoxyalkenyl," refers to a loweralkoxy group attached to the parent molecular group through an alkenyl group.

The term "alkoxyalkoxy," refers to a loweralkoxy group attached to the parent molecular group through a loweralkoxy group.

The term "alkoxyalkyl," refers to a loweralkoxy group attached to the parent molecular group through a loweralkyl group.

The term "alkoxycarbonyl," refers to an ester group; e.g., an alkoxy group attached to the parent molecular group through a carbonyl.

The term "alkoxycarbonylalkyl," refers to an alkoxycarbonyl group attached to the parent molecular group through a loweralkyl group.

The term "alkoxycarbonylalkenyl," refers to an alkoxycarbonyl group attached to the parent molecular group through an alkenyl group.

The term "alkoxycarbonylalkoxy," refers to an alkoxycarbonyl group attached to the parent molecular group through a loweralkoxy group.

The term "alkenyl," refers to a monovalent straight or branched chain hydrocarbon radical having from two to six carbons and at least one carbon—carbon double bond.

The term "alkyl," refers to a saturated, monovalent straight or branched chain hydrocarbon having from one to twenty carbons.

The term "alkylsulfonyl," refers to a loweralkyl group attached to the parent molecular group through a sulfonyl.

The term "alkynyl," refers to a monovalent straight or branched chain hydrocarbon group having from two to six carbons and at least one carbon—carbon triple bond.

The term "amino," refers to —NR$^9$R$^{10}$, wherein R$^9$ and R$^{10}$ are independently selected from hydrogen, loweralkyl, aryl, arylalkyl, cycloalkyl, cycloalkylalkyl, heteroaryl, heteroarylalkyl, heterocycle, (heterocycle)alkyl, carboxycarbonyl, and an amino protecting group.

The term "aminoalkyl," refers to an amino group attached to the parent molecular group through a loweralkyl group.

The term "aminosulfonyl," refers to an amino group attached to the parent molecular group through a sulfonyl.

The terms "amino protecting group," or "nitrogen protecting group," refer to selectively introducible and removable groups which protect amino groups against undesirable side reactions during synthetic procedures. Examples of amino protecting groups include methoxycarbonyl, ethoxycarbonyl, trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, isopropoxycarbonyl, phthaloyl, succinyl, benzyl, diphenylmethyl, triphenylmethyl (trityl), methylsulfonyl, phenylsulfonyl, para-toluenesulfonyl, trimethylsilyl, triethylsilyl, triphenylsilyl, and the like. Preferred nitrogen protecting groups of the invention are benzyloxycarbonyl (Cbz), formyl, acetyl, methylsulfonyl, benzoyl, and phenylsulfonyl.

The term "aryl," refers to an aromatic, carbocyclic ring or two fused aromatic, carbocyclic rings. These groups are exemplified by phenyl and naphthyl. The aryl groups of the invention can be optionally substituted with one, two, three, four, or five substituents independently selected from loweralkyl, alkenyl, alkynyl, alkoxy, alkanoyl, alkanoyloxy, alkoxycarbonyl, alkylsulfonyl, amino, aminosulfonyl, azido, carboxamido, carboxy, cyano, halo, hydroxy, nitro, perfluoroalkyl, perfluoroalkoxy, oxo, thioalkoxy, phenyl, heteroaryl selected from furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, and triazinyl, and heterocycle selected from tetrahydrofuranyl, piperidinyl, piperazinyl, morpholinyl, and thiomorpholinyl. The phenyl, the heteroaryl, and the heterocycle groups optionally substituting the aryl groups of the invention are attached to the parent aryl groups through either a covelent bond, a loweralkyl, an oxygen atom, or a carbonyl. The phenyl, the heteroaryl, and the heterocycle groups optionally substituting the aryl groups of the invention can also be further substituted with one, two, or three substituents independently selected from loweralkyl, loweralkoxy, carboxyl, azido, carboxaldehyde, halo, hydroxy, perfluoroalkyl, and perfluoroalkoxy.

The term "arylboronic acid," refers to an aryl group to which is attached —B(OH)$_2$.

The term "aryl trialkylstannane," refers to an aryl group to which is attached —Sn(R$^{12}$)$_3$, wherein each R$^{12}$ is independently selected from loweralkyl.

The term "arylalkenyl," refers to an aryl group, attached to the parent molecular group through an alkenyl group.

The term "arylalkyl," refers to an aryl group attached to the parent molecular group through a loweralkyl group. The loweralkylene part of the arylalkyl group can be optionally substituted with a substituent selected from alkoxycarbonyl, hydroxy, carboxy, and alkanoyloxy.

The term "arylalkoxy," refers to an aryl group attached to the parent molecular group through a loweralkoxy group.

The term "azido," refers to —N$_3$.

The term "carbonyl," refers to —C(O)—.

The term "carboxamido," refers to an amide; e.g., an amino group attached to the parent molecular group through a carbonyl.

The term "carboxamidoalkenyl," refers to a carboxamido group attached to the parent molecular group through an alkenyl group.

The term "carboxamidoalkyl," refers to a carboxamido group attached to the parent molecular group through a loweralkyl group.

The term "carboxy," refers to —CO$_2$H. The carboxy groups of the invention can be optionally protected by the replacement of the hydrogen atom thereof by a carboxy protecting group.

The term "carboxaldehyde," refers to —CHO.

The term "carboxy," refers to —CO$_2$H. The carboxy groups of the invention can be optionally protected by the replacement of the hydrogen atom thereof by a carboxy protecting group.

The term "carboxyalkoxy," refers to a carboxy group attached to the parent molecular group through an alkoxy group.

The term "carboxycarbonyl," refers to a carboxy group connected to the parent molecular group through a carbonyl.

The term "carboxy protecting group," refers to selectively introducible and removable groups which protect carboxyl groups against undesirable side reactions during synthetic procedures and includes all conventional carboxyl protecting groups. Examples of carboxyl groups include loweralkyl, phenyl, naphthyl, benzyl, diphenylmethyl, triphenylmethyl (trityl), para-nitrobenzyl, para-methoxybenzyl, acetylmethyl, benzoylmethyl, para-nitrobenzoylmethyl, para-bromobenzoylmethyl, 2-tetrahydropyranyl 2-tetrahydrofuranyl, 2,2,2-trichloroethyl cyclopropyl, cyclobutyl, cyclopentyl, cyclohexyl, methoxymethyl, methoxyethoxymethyl, arylalkoxyalkyl benzyloxymethyl 1,1-dimethyl-2-propenyl, 3-methyl-3-butenyl, allyl, and the like. Preferred carboxyl protecting groups of the invention are lowerlkyl.

The term "cyano," refers to —CN.

The term "cycloalkenyl," refers to a monovalent cyclic or bicyclic hydrocarbon of four to twelve carbons having at least one carbon—carbon double bond.

The term "cycloalkenylalkyl," refers to a cycloalkenyl group attached to the parent molecular group through a loweralkyl group.

The term "cycloalkyl," refers to a monovalent saturated cyclic or bicyclic hydrocarbon group of three to twelve carbons. The cycloalkyl groups of the invention can be optionally substituted with one, two, three, or four substituents independently selected from loweralkyl, amino, alkoxy, alkoxycarbonyl, carboxaldehyde, carboxyl, halo, hydroxy, phenyl, heteroaryl, heterocycle, and oxo.

The term "cycloalkylalkyl," refers to a cycloalkyl group attached to the parent molecular group through a loweralkyl group.

The term "halo," refers to F, Cl, Br, or I.

The term "haloalkyl," refers to a halo group attached to the parent molecular group through a loweralkyl group.

The term "heteroaryl," refers to cyclic, aromatic groups having five or six atoms, wherein at least one atom is selected from nitrogen, oxygen, and sulfur, and the remaining atoms are carbon. The five-membered rings have two double bonds, and the six-membered rings have three double bonds. Heteroaryls of the invention are exemplified by furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of the invention are connected to the parent molecular group through a carbon atom in the ring or, as exemplified by imidazole and pyrazolyl, through either a carbon atom or nitrogen atom in the ring. The heteroaryl groups of the invention can be optionally substituted with one, two, or three radicals independently selected from loweralkyl, alkenyl, alkynyl, alkoxy, alkanoyl, alkanoyloxy, alkoxycarbonyl, alkylsulfonyl, amino, aminosulfonyl, azido, carboxamido, carboxy, cyano, halo, hydroxy, nitro, perfluoroalkyl, perfluoroalkoxy, oxo, thioalkoxy, a nitrogen protecting group, phenyl, and a heterocycle selected from tetrahydrofuranyl, piperidinyl, piperazinyl, morpholinyl, and thiomorpholinyl. The phenyl and the heterocycle groups optionally substituting the heteroaryl groups of the invention are attached to the heteroaryl through either a covelent bond, a loweralkyl group, an oxygen, or a carbonyl group. The phenyl and the heterocycle groups optionally substituting the heteroaryl groups of the invention can also be further substituted with one, two, or three substituents independently selected from loweralkyl, loweralkoxy, carboxyl, azido, carboxaldehyde, halo, hydroxy, perfluoroalkyl, and perfluoroalkoxy. The heteroaryl groups of the invention can also be fused to one or two phenyl rings, in which case the heteroaryl group can be connected to the parent molecular group through either the heteroaryl part or the phenyl part of the fused ring system. Heteroaryl groups of this type are exemplified by quinolinyl, isoquinolinyl, benzodioxolyl, benzodioxinyl, dibenzo(b,d)furan, indolyl, and the like.

The term "heteroarylalkoxy," refers to a heteroaryl attached to the parent molecular group through an alkoxy group.

The term "heteroarylalkyl," refers to a heteroaryl group attached to the parent molecular group through a loweralkyl group.

The term "heteroarylalkenyl," refers to a heteroaryl group attached to the parent molecular group through an alkenyl group.

The term "heteroarylboronic acid," refers to a heteroaryl group to which is attached —$B(OH)_2$.

The term "heteroaryl trialkylstannane," refers to a heteroaryl group to which is attached —$Sn(R^{12})_3$, wherein $R^{12}$ is defined herein.

The term "heteroarylthioxy," refers to a heteroaryl attached to the parent molecular group through a sulfur atom.

The term "heteroarylthioxyalkyl," refers to a heteroarylthioxy group attached to the parent molecular group through a loweralkyl group.

The term "heterocycle," refers to cyclic, non-aromatic, four-, five-, or six-membered groups containing at least one atom selected from oxygen, nitrogen, and sulfur. The four-membered rings have zero double bonds, the five-membered rings have zero or one double bonds, and the six-membered rings have zero, one, or two double bonds. Heterocycle groups of the invention are exemplified by dihydropyridinyl, imidazolinyl, morpholinyl, piperazinyl, pyrrolidinyl, pyrazolidinyl, tetrahydropyridinyl, piperidinyl, thiomorpholinyl, 1,3-dioxolanyl, 1,4-dioxanyl, 1,3-dioxanyl, and the like. The heterocycles of the invention are attached to the parent molecular group through a carbon atom or nitrogen atom in the ring. The heterocycles of the invention can be optionally substituted one, two, or three substituents independently selected from loweralkyl, loweralkoxy, alkanoyl, alkanoyloxy, alkoxycarbonyl, alkylsulfonyl, amino, aminosulfonyl, azido, carboxamido, carboxy, cyano, halo, hydroxy, a nitrogen protecting group, perfluoroalkyl, perfluoroalkoxy, oxo, phenyl, and heteroaryl selected from furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, and triazinyl. The phenyl and the heteroaryl groups optionally substituting the heterocycles of the invention are attached through a covelent bond, a loweralkyl group, an oxygen atom, or a carbonyl. The phenyl and the heteroaryl groups optionally substituting the heterocycles of the invention can also be further substituted with one, two, or three substituents independently selected from loweralkyl, loweralkoxy, carboxyl, azido, carboxaldehyde, halo, hydroxy, perfluoroalkyl, and perfluoroalkoxy. The heterocycles of the invention can also be optionally fused to one or two phenyl rings, in which case the heterocycle can be connected to the parent molecular group through either the heterocycle part or the phenyl part of the fused ring system. Heterocycle groups of this type are exemplified by 1,3-benzodioxanyl, 1,3-benzodioxolyl, 2,4-dihydro-2H-1,4-benzoxazinyl, 1,3-benzothiazole, isoindoline, and the like.

The term "(heterocycle)alkyl," refers to a heterocycle attached to the parent molecular group through a loweralkyl group.

The term "hydroxy," refers to —OH. The hydroxy groups of the invention can be optionally protected by replacement of the hydrogen atom thereof with a hydroxy protecting group.

The term "hydroxyalkyl," refers to a hydroxyl group attached to the parent molecular group through a loweralkyl group.

The term "hydroxy protecting group," refers to selectively introducible and removable groups which protect hydroxy groups against undesirable side reactions during synthetic procedures. Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, tert-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like.

The term "loweralkoxy," refers to a loweralkyl group attached to the parent molecular group through an oxygen atom.

The term "loweralkyl," refers to a saturated, monovalent straight or branched chain hydrocarbon having from one to six carbons.

The term "loweralkylene," refers to a divalent straight or branched chain saturated hydrocarbon diradical having from one to six carbons.

The term "nitro," refers to —$NO_2$.

The term "oxo," refers to a group formed by the replacement of two hydrogen atoms on the same carbon atom with a single oxygen atom.

The term "perfluoroalkoxy," refers to a perfluoroalkyl group attached to the parent group through an oxygen atom.

The term "perfluoroalkyl," refers to a loweralkyl group in which all of the hydrogen atoms have been replaced with fluoride atoms.

The instant compounds can exist as therapeutically acceptable salts. The term "therapeutically acceptable salt," refers to salts or zwitterions of the compounds which are water or oil-soluble or dispersible, suitable for treatment of diseases without undue toxicity, irritation, and allergic response, commensurate with a reasonable benefit/risk ratio, and effective for their intended use. The salts can be prepared during the final isolation and purification of the compounds or separately by reacting the amino group of the compounds with a suitable acid. Representative salts include acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalic, maleic, pivalate, propionate, succinate, tartrate, trichloroacetic, trifluoroacetic, glutamate, paratoluenesulfonate, undecanoate, hydrochloric, hydrobromic, sulphuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the instant compounds by reaction the carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the instant invention.

The instant compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The term "prodrug," refers to compounds which are rapidly transformed in vivo to parent compounds of formulas (I)–(VI) for example, by hydrolysis in blood.

The term "sulfonyl," refers to —$SO_2$—.

The term "thioalkoxy," refers to a loweralkyl group attached to the parent molecular group through a sulfur atom.

Asymmetric centers can exist in the instant compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the instant compounds The invention contemplates the various geometric isomers and mixtures thereof resulting from the disposal of substituents around a carbon—carbon double bond, a cycloalkyl, or a heterocycle. Substituents around a carbon—carbon double bond are designated as being of Z or E configuration and substituents around a cycloalkyl or heterocycle are designated as being of cis or trans configuration.

Therapeutic compositions of the instant compounds comprise an effective amount of the same formulated with one or more therapeutically acceptable excipients. The term "therapeutically acceptable excipient," refers to a non-toxic, solid, semi-solid or liquid filler, diluent, encapsulating material, or formulation auxiliary of any type. Examples of therapeutically acceptable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the instant compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the instant compounds comprise sterile, injectable, aqueous and oleaginous solutions, suspensions or emulsions, any of which can be optionally formulated with parenterally acceptable diluents, dispersing, wetting, or suspending agents. These injectable preparations can be sterilized by filtration through a bacterial-retaining filter or formulated with sterilizing agents which dissolve or disperse in the injectable media.

PTP inhibition by the instant compounds can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the instant compounds include capsules, tablets, pills, powders, and granules. In such forms, the compound is mixed with at least one inert, therapeutically acceptable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable nonirritating excipient which is solid at ordinary temperature but fluid in the rectum.

The instant compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the instant compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Diseases caused or exacerbated by protein tyrosine phosphatase PTP1B activity are treated or prevented in a patient by administering to the same a therapeutically effective amount of the instant compounds in such an amount and for such time as is necessary to achieve the desired result. The term "therapeutically effective amount," refers to a sufficient amount of the compound to treat protein tyrosine phosphatase PTP1B activity at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the instant compounds in single or divided doses can be in amounts, for example, from 0.01 to 50 mg/kg body weight or more usually from 0.1 to 25 mg/kg body weight. Single dose compositions can contain such amounts or submultiples thereof of the compounds to make up the daily dose. In general, treatment regimens comprise administration to a patient in need of such treatment from about 10 mg to about 1000 mg of the compounds per day in single or multiple doses.

Specific compounds of the invention include, but are not limited to,

- ((2-(4-bromophenyl)-2-cyclohexylethyl)amino)(oxo)acetic acid,
- (benzyl(2-(4-bromophenyl)-2-cyclohexylethyl)amino)-(oxo)acetic acid,
- (((4-bromophenyl)(cyclohexyl)methoxy)amino)(oxo)acetic acid,
- ((cyclohexyl(3-(2-quinolinyl)phenyl)methoxy)amino)(oxo)acetic acid,
- (benzyl(2,3-dichloro-4-(1-naphthyl)benzyl)amino) (oxo)acetic acid,
- N-benzyl-2-hydroxy-N-((4,1'-binaphth-1-yl)methyl)-amino)(oxo)acetic acid,
- (benzyl(2-chloro-4-(1-naphthyl)benzyl)amino)(oxo)acetic acid,
- (benzyl((4-bromo-5-(1-naphthyl)-2-thienyl)methyl)-amino)(oxo)acetic acid,
- (benzyl((5-(1-naphthyl)-2-thienyl)methyl)amino)-(oxo)acetic acid,
- (benzyl(4-(2-quinolinylmethoxy)benzyl)amino)(oxo)acetic acid,
- oxo((2-phenylethyl)(4-(2-quinolinylmethoxy)benzyl)-amino)acetic acid,
- (cyclohexyl(4-(2-quinolinylmethoxy)benzyl)amino)-(oxo)acetic acid,
- (benzyl(2-methoxy-4-(1-naphthyl)benzyl)amino)-(oxo)acetic acid,
- ((2-hydroxyethyl)((4,1'-binaphth-1-yl)methyl)amino)-(oxo)acetic acid,
- ((2-cyclohexyl-2-(4-(1-naphthyl)phenyl)ethyl)(2-(4-morpholinyl)ethyl)amino)(oxo)acetic acid,
- (benzyl(2-cyclohexyl-2-(4-(1-naphthyl)phenyl)ethyl)-amino)(oxo)acetic acid,
- ((2-cyclohexyl-2-(4-(1-naphthyl)phenyl)ethyl)(2-phenylethyl)amino)(oxo)acetic acid,
- ((2-cyclohexyl-2-(4-(1-naphthyl)phenyl)ethyl)(2-(3,4-dimethoxyphenyl)ethyl)amino)(oxo)acetic acid,
- (benzyl(2-(carboxymethoxy)-4-(1-naphthyl)benzyl)amino)-(oxo)acetic acid,
- (benzyl(2-(2-tert-butoxy-2-oxoethoxy)-4-(1-naphthyl)-benzyl)amino)(oxo)acetic acid,
- 3-(((2-((benzyl(carboxycarbonyl)amino)methyl)-5-(1-naphthyl)phenoxy)acetyl)amino)benzoic acid,
- (benzyl(2-(2-(((4-(methoxycarbonyl)cyclohexyl)methyl)-amino)-2-oxoethoxy)-4-(1-naphthyl)benzyl)amino)(oxo)acetic acid,
- (benzyl(4-(1-naphthyl)-2-(2-oxo-2-((3-(2-oxo-1-pyrrolidinyl)propyl)amino)ethoxy)benzyl)amino)(oxo)acetic acid,
- 5-((2-((benzyl(carboxycarbonyl)amino)methyl)-5-(1-naphthyl)-phenoxy)methyl)-2-furoic acid,
- ((cyclohexyl(4-(2-quinolinylmethoxy)phenyl)methyl)-amino)(oxo)acetic acid,
- ((2-methoxy-4-(1-naphthyl)benzyl)(2-phenylethyl)amino)-(oxo)acetic acid,
- ((2,3-dichloro-4-(1-naphthyl)benzyl)(2-phenylethyl)amino)(oxo)acetic acid,
- ((2-(4-(((carboxycarbonyl)amino)sulfonyl)phenyl)-ethyl)(2-cyclohexyl-2-(4-(1-naphthyl)phenyl)ethyl)amino)-(oxo)acetic acid,
- ((2-cyclohexyl-2-(4-(1-naphthyl)phenyl)ethyl)(3-(2-oxo-1-pyrrolidinyl)propyl)amino)(oxo)acetic acid,
- (benzyl((5-(1-naphthyl)(1,1'-biphenyl)-2-yl)methyl)-amino)(oxo)acetic acid,
- (benzyl((4'-formyl-5-(1-naphthyl)(1,1'-biphenyl)-2-yl)-methyl)amino)(oxo)acetic acid,
- (benzyl(2-((1E)-3-tert-butoxy-3-oxo-1-propenyl)-4-(1-naphthyl)benzyl)amino)(oxo)acetic acid,
- (2E)-3-(2-((benzyl(carboxycarbonyl)amino)methyl)-5-(1-naphthyl)phenyl)-2-propenoic acid,
- (benzyl(2-(4-((1E)-3-tert-butoxy-3-oxo-1-propenyl)-phenyl)-2-cyclohexylethyl)amino)(oxo)acetic acid,
- ((2,3-dichloro-4-(1-naphthyl)benzyl)(2-(1,3-dioxo-1,3-dihydro-2H-isoindol-2-yl)ethyl)amino)(oxo)acetic acid,
- (((1,1'-biphenyl)-4-yl(cyclohexyl)methoxy)amino)-(oxo)acetic acid,
- (benzyl(4-(1-naphthyl)-2-((1E)-3-oxo-3-((3-(2-oxo-1-pyrrolidinyl)propyl)amino)-1-propenyl)benzyl)amino)-(oxo)acetic acid,
- (2E)-3-(4-(2-(benzyl(carboxycarbonyl)amino)-1-cyclohexyl-ethyl)phenyl)-2-propenoic acid,
- (benzyl(2-cyclohexyl-2-(4-((1E)-3-(4-hydroxy-3,5-diphenyl-anilino)-3-oxo-1-propenyl)phenyl)ethyl)amino)-(oxo)acetic acid,
- (benzyl(2-cyclohexyl-2-(4-(3-(4-hydroxy-3,5-diphenyl-anilino)-3-oxopropyl)phenyl}ethyl)amino)(oxo)acetic acid,
- ((2-(1-(tert-butoxycarbonyl)-4-piperidinyl)-2-(4-(1-naphthyl)phenyl)ethyl)(2-phenylethyl)amino)(oxo)acetic acid,
- (benzyl(2-cyclohexyl-2-(3'-phenyl(1,1'-biphenyl)-4-yl)-ethyl)amino)(oxo)acetic acid,
- (benzyl(2-cyclohexyl-2-(4-dibenzo(b,d)furan-2-ylphenyl)ethyl)amino)(oxo)acetic acid,
- (benzyl(2-cyclohexyl-2-(4-(8-quinolinyl)phenyl)ethyl)-amino)(oxo)acetic acid,
- (benzyl(2-cyclohexyl-2-(4-(2,3-dihydro-1,4-benzodioxin-6-yl)phenyl)ethyl)amino)(oxo)acetic acid, ((2-(4-(1-naphthyl)phenyl)-2-(4-piperidinyl)ethyl)(2-phenyl-ethyl)amino)(oxo)acetic acid trifluoroacetate, ((2-(1-acetyl-4-piperidinyl)-2-(4-(1-naphthyl)-phenyl)ethyl)-(2-phenylethyl)amino)(oxo)acetic acid, ((2-(1-(methylsulfonyl)-4-piperidinyl)-2-(4-(1-naphthyl)-phenyl)ethyl)(2-phenylethyl)amino)(oxo)acetic acid, ((2-(1-benzoyl-4-piperidinyl)-2-(4-(1-naphthyl)phenyl)-ethyl)(2-phenylethyl)amino)(oxo)acetic acid, ((2-(4-(1-naphthyl)phenyl)-2-(1-(phenylsulfonyl)-4-piperidinyl)ethyl)(2-phenylethyl)amino)(oxo)acetic acid, ((2-(1-(2-(diethylamino)-2-oxoethyl)-4-piperidinyl)-2-(4-(1-naphthyl)phenyl)ethyl)(2-phenylethyl)amino)(oxo)acetic acid, 5-((4-(2-((carboxycarbonyl)(2-phenylethyl)amino)-1-(4-(1-naphthyl)phenyl)ethyl)-1-piperidinyl)methyl)-2-furoic acid, ((2-cyclohexyl-2-(4-(1-naphthyl)phenyl)ethyl)(2-((5-nitro-2-pyridinyl)amino)ethyl)amino)(oxo)acetic acid, ((2-cyclohexyl-2-(4-(1-naphthyl)phenyl)ethyl)(2-(1-pyrrolidinyl)ethyl)amino)(oxo)acetic acid, ((2-cyclohexyl-2-(4-(1-naphthyl)phenyl)ethyl)(2-(1H-indol-3-yl)ethyl)amino)(oxo)acetic acid, ((2-cyclohexyl-2-(4-(1-naphthyl)phenyl)ethyl)(2-hydroxy-2-phenylethyl)amino)(oxo)acetic acid, (((1S)-1-benzyl-2-hydroxyethyl)(2-cyclohexyl-2-(4-(1-naphthyl)phenyl)ethyl)amino)-(oxo)acetic acid, (2S)-2-((carboxycarbonyl)(2-cyclohexyl-2-(4-(1-naphthyl)-phenyl)ethyl)amino)-3-phenylpropanoic acid, (benzyl(2-(4-((1E)-3-((1,1'-biphenyl)-4-ylamino)-3-oxo-1-propenyl)phenyl)-2-cyclohexylethyl)amino)(oxo)acetic acid, (benzyl(2-cyclohexyl-2-(4-((1E)-3-(3,5-ditert-butyl-anilino)-3-oxo-1-propenyl)phenyl)ethyl)amino)(oxo)acetic acid, (benzyl(2-cyclohexyl-2-(4-((1E)-3-oxo-3-(4-phenoxyanilino)-1-propenyl)phenyl)ethyl)amino)(oxo)acetic acid, (benzyl(2-cyclohexyl-2-(4-((1E)-3-(4-(2,3-dimethylphenyl)-1-piperazinyl)-3-oxo-1-propenyl)phenyl)-ethyl)amino)(oxo)acetic acid, ((2-(4-((1E)-3-(4-benzhydryl-1-piperazinyl)-3-oxo-1-propenyl)phenyl)-2-cyclohexylethyl)(benzyl)amino)(oxo)acetic acid, oxo((2-phenylethyl)((4,1'-binaphth-1-yl)methyl)amino)-acetic acid, (((4-((1,3-benzothiazol-2-ylsulfanyl)methyl)phenyl)-(cyclohexyl)methoxy)amino)(oxo)acetic acid, ((cyclohexyl(4-(2,3-dihydro-1,4-benzodioxin-6-yl)-phenyl)methoxy)amino)(oxo)acetic acid, (((4-(decyloxy)-1-naphthyl)methyl)(2-phenylethyl)-amino)(oxo)acetic acid, (((4-(octadecyloxy)-1-naphthyl)methyl)(2-phenylethyl)-amino)(oxo)acetic acid, ((2-(1,1'-biphenyl)-3-yl-2-cyclohexylethyl)(2-phenyl-ethyl)amino)(oxo)acetic acid, (((4-butoxy-1-naphthyl)methyl)(2-phenylethyl)amino)-(oxo)acetic acid, oxo((2-phenylethyl)((4-(tetradecyloxy)-1-naphthyl)-methyl)amino)acetic acid, ((2-cyclohexyl-2-(3-(1-naphthyl)phenyl)ethyl)(2-phenyl-ethyl)amino)(oxo)acetic acid, ((2-cyclohexyl-2-(3-(2-naphthyl)phenyl)ethyl)(2-phenyl-ethyl)amino)(oxo)acetic acid, and ((2-cyclohexyl-2-(3'-phenyl(1,1'-biphenyl)-3-yl)-ethyl)(2-phenylethyl)amino)(oxo)acetic acid.

Determination of Biological Activity

Purification of Human Protein Tyrosine Phosphatase PTP1B from *E. coli*

Human protein tyrosine phosphatase PTP1B (1-321) was expressed in *E. coli* BL21(DE3). The cell paste was resuspended in 4 cell paste volumes of lysis buffer containing 100 mM MES (pH 6.5), 100 mM NaCl, 1 mM EDTA, 1 mM DTT, 1 mM PMSF, 20 U/mL Benzonase, 0.5 mg/mL lysozyme, and 1 mM $MgCl_2$ and incubated for 35 minutes at room temperature. The cells were lysed at 11,000 psi using a Rannie homogenizer, and the homogenate was clarified in a Beckman GSA rotor at 10,000×g for 30 minutes at 4° C. The supernatant was loaded onto a 5×21 cm S-Sepharose-FF column (Amersham Pharmacia Biotech) preequilibrated with 5 column volumes of buffer containing 100 mM MES (pH 6.5), 100 mM NaCl, 1 mM EDTA, and 1 mM DTT and eluted with 10 column volumes of the same. The fractions (28 mL each) were assayed for protein by 10–20% Tris-Glycine SDS-PAGE. Fractions which contained >95% protein tyrosine phosphatase PTP1B were combined.

Protein Tyrosine Phosphatase PTP1B Activity Assay

Protein tyrosine phosphatase PTP1B activity was determined by measuring the phosphate release from triphosphorylated peptide which corresponds to residues 1135–1156 of the b-subunit of the human insulin receptor (bIRK substrate) as described in *Nature*, 313, 756–761 (1985). Protein tyrosine phosphatase PTP1B activity was determined in a final assay volume of 50 µL containing 50 mM Tris HCl, 50 mM Tris Base, 150 mM NaCl, 3 mM DTT, 0.1 mg/mL bovine serum albumin (Sigma), 2 nM protein tyrosine phosphatase PTP1B(1-321), and 16 µM bIRK substrate. Various concentrations of test compounds in 5 µL of 10% DMSO were incubated for 5 minutes at room temperature with 20 µL of protein tyrosine phosphatase PTP1B enzyme in a flat-bottom microtiter plate (Costar). The phosphatase reaction was initiated by the addition of bIRK substrate (25 µL) and proceeded for 10 minutes at room temperature. The reaction was terminated by the addition of 100 µL of malachite green (Upstate Biotechnology Inc.) containing 0.01% Tween-20. After a 5 minute incubation, quantitation of free phosphate released from the bIRK substrate was determined in a Beckman Biomek Plate Reader by measuring the absorbence of the malachite green at 650 nm.

The instant compounds were found to inhibit protein tyrosine phosphatase PTP1B with inhibitory potencies in a range of about of about 3 µM to about 100 µM. In a preferred range, the compounds inhibited protein tyrosine phosphatase PTP1B with inhibitory potencies in a range of about of about 29 µM to about 60 µM; and in a more preferred range, the compounds inhibited protein tyrosine phosphatase PTP1B with inhibitory potencies in a range of about of about 3 µM to about 21 µM.

As protein tyrosine phosphatase PTP1B inhibitors, therefore, the instant compounds are useful for treating diseases caused by overexpressed or altered protein tyrosine phosphatase PTP1B activity. These diseases include autoimmune diseases, acute and chronic inflammatory diseases, osteoporosis, obesity, cancer, malignant diseases, type I and type II diabetes.

Synthetic Methods

The compounds and processes of the instant invention will be better understood in connection with the following synthetic schemes which illustrate methods by which the compounds can be prepared. The compounds can be prepared by a number of synthetic procedures, and representative procedures are shown in Schemes 1–6. The groups A, B, d, $L^1$, $L^2$, $R^1$, $R^2$, $R^3$, and $R^4$, are previously defined, and the groups $X^1$ and $X^2$ are define below. It will be appreciated by a skilled practitioner that selective protection and deprotection steps can be conducted, depending on the nature of A, B, d, $L^1$, $L^2$, $R^1$, $R^2$, $R^3$, and $R^4$, to successfully complete the syntheses of the compounds. A discussion of protecting groups is provided in Greene and Wuts, "Protective Groups in Organic Synthesis," 3rd Ed., John Wiley & Son, Inc., (1999). It will also be appreciated that the compounds can be synthesized by substitution of the appropriate reactants and reagents and that the steps themselves can be conducted in varying order. A discussion of functional group transformations is provided in Larock, "Comprehensive Organic Transformations. A Guide to Functional Group Preparations," 2nd. Ed., John Wiley & Sons, Inc. New York (1999).

Abbreviations

Abbreviations used in the descriptions of the schemes and the examples that follow are: dba for dibenzylidine acetone; DCI for direct chemical ionization; DEAD for diethyl azodicarboxylate; DIAD for diisopropyl azodicarboxylate; DIBAL-H for diisobutylaluminum hydride; DME for dimethoxyethane; DMF for N,N-dimethylformamide; DMSO for dimethylsulfoxide; EDCI for 1-(3-(dimethylamino)propyl)-3-ethylcarbodiimide hydrochloride; ESI for electrospray chemical ionization; HMPA for hexamethylphosphoramide; MTBE for methyl tert-butyl ether; TFA for trifluoroacetic acid; THF for tetrahydrofuran; TLC for thin layer chromatography; py for pyridine; and Ts for para-toluenesulfonyl.

Scheme 1

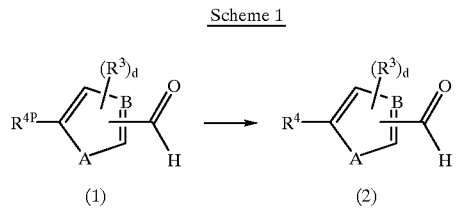

As shown in Scheme 1, compounds of formula (1) wherein $R^{4P}$ is an $R^4$ precursor such as hydroxy, triflate, bromo, or iodo, can be converted to compounds of formula (2) by treatment of the former with coupling partners.

The compounds of formula (1) are commercially available or can be prepared by means well-known in the art, such as, for example, deprotonation of the corresponding aryl or heteroaryl group with a base such as lithium bis (trimethylsilyl)amide, sodium bis(trimethylsilyl)amide, potassium bis(trimethylsilyl)amide, n-butyllithium, sec-butyllithium, tert-butyllithium, or lithium diisopropylamide and treatment of the resulting anion with a reagent which introduces the desired functionality. For example, treatment of the anion with DMF will introduce a carboxaldehyde group at the first deprotonation site; treatment of the anion with electrophilic halogenating reagents such as bromine, N-bromosuccinimide, iodine, or N-iodosuccinimide will introduce the corresponding halide that site; treatment of the anion with an oxidizing agent such as $MoO_5$.py.HMPA will introduce a hydroxy group at that site; and treatment of the anion with electrophilic nitrogen reagents such as $ClNH_2$, $(C_6H_5)_2P(O)NH_2$, $Br_2/NaN_3$, and $TsN_3$. The substitution pattern of carboxaldehyde and $R^{4P}$ on what will become the proximal ring of the instant compounds can be predetermined by the different acidities of the protons on the aryl or heteroaryl ring starting materials and the strength of the base used for the deprotination. Subsequent deprotonation and derivitization reactions can be accomplished by treatment of the starting material with a second equivalent of base followed by treatment of the anion with the appropriate electrophile.

When $R^{4P}$ is bromo, iodo, or triflate, the coupling partners comprise substituted alkenes, optionally substituted arylboronic acids, optionally substituted heteroarylboronic acids, optionally substituted aryl trialkylstannanes, and optionally substituted heteroaryl trialkylstannanes. The reactions are conducted with a base such as cesium fluoride, sodium carbonate, or potassium carbonate and palladium catalysts such as $Pd(PPh_3)_4$, $Pd(PPh_3)_2Cl_2$, or $Pd_2(dba)_3$ in solvents such as acetonitrile, THF, DME, DMF, benzene, toluene, or mixtures thereof at temperatures of about 25° C. to about 120° C. The reagents and reaction conditions selected depend on the nature of the coupling partners. The reaction times are typically about 1 to about 18 hours.

When $R^{4P}$ is hydroxy, the coupling partners comprise optionally substituted alkyl halides in the presence of a base such as sodium hydride or potassium hydride at reaction temperatures are about 0° C. to about 50° C. The reaction times are typically about 1 to about 18 hours.

Elaboration of $R^{4P}$ to compounds wherein $R^4$ is $R^7$-T- can be accomplished by treatment of the appropriately substituted starting material with the corresponding isocyanates, chloroformates, acid halides, and carbamoyl chlorides. The reagents, solvents, and reaction conditions such as temperatures and reaction times for these transformations are well-known in the art.

Scheme 2

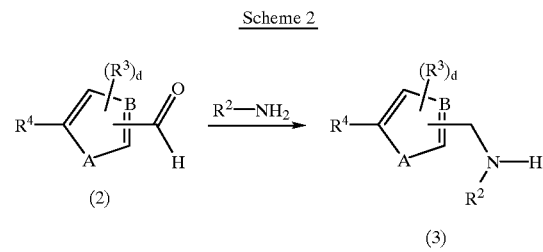

As shown in Scheme 2, compounds of formula (2) can be converted to compounds of formula (3) by treatment of the former with amines in the presence of reducing agents. Representative reducing agents include sodium triacetoxyborohydride, sodium borohydride, and sodium cyanoborohydride. The reactions are conducted in solvents such as methanol, ethanol, isopropanol, or mixtures thereof at temperatures of about 0° C. to about 30° C. Reaction times are typically about 1 to about 24 hours.

Scheme 3

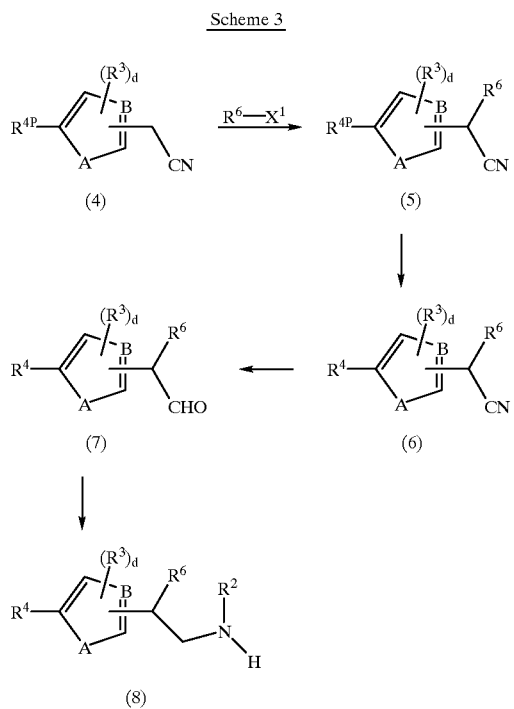

As shown in Scheme 3, compounds of formula (4) can be converted to compounds of formula (5) by treatment of the former with base and compounds of formula $R^6$—$X^1$, wherein $X^1$ represents a leaving group such as halide, sulfonate, or triflate. Representative bases include sodium hydride, potassium hydride, lithium hexamethyldisilazide, sodium hexamethyldisilazide, potassium hexamethyldisilazide, and LDA. Solvents used in these reactions include THF, DMF, DMSO, MTBE, diethyl ether, or mixtures thereof. The reaction temperatures are about 0° C. to 30° C. and depend on the method chosen. Reaction times are typically about 1 to about 12 hours.

Compounds of formula (5) can be converted to compounds of formula (6) using the conditions described for the conversion of compounds of formula (1) to compounds of formula (2) as described in in Scheme 1.

Compounds of formula (6) can be converted to compounds of formula (7) by treatment of the former with reducing agents followed by hydrolysis with aqueous acid. Representative reducing agents include $SnCl_2$/HCl lithium aluminum hydride, and DIBAL-H. Representative acids include HCl, HBr, TFA, or mixtures thereof. Examples of solvents used in these reactions include toluene, THF, and hexanes. The reaction temperatures are about −78° C. to about 0° C. and depend on the method chosen.

Compounds of formula (7) can be converted to compounds of formula (8) using the conditions described for the conversion of compounds of formula (2) to compounds of formula (3) as described in in Scheme 2.

Scheme 4

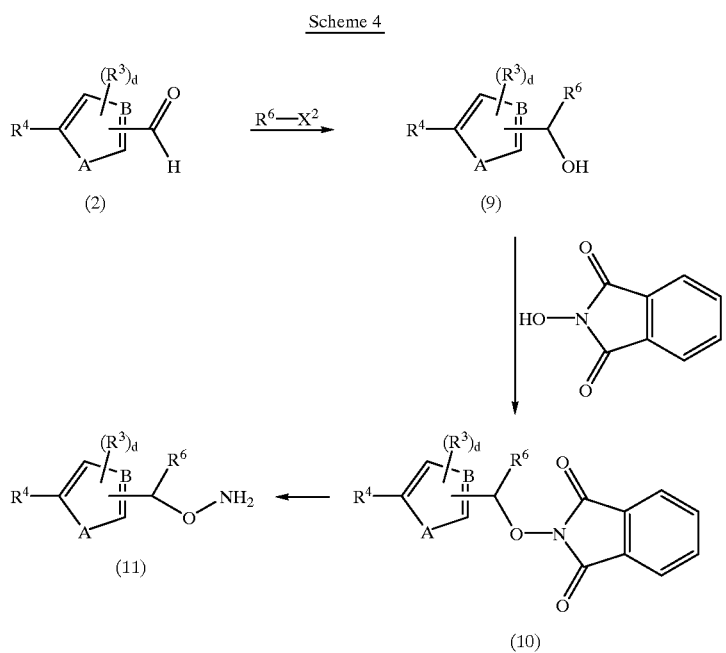

As shown in Scheme 4, compounds of formula (2) can be converted to compounds of formula (9) by treatment with compounds of formula $R^6$—$X^2$, wherein $X^2$ represents lithium, magnesium halide, and zinc halide. Examples of solvents used in these reactions include THF, MTBE, diethyl ether, and mixtures thereof. Reaction temperatures are about −78° C. to about 25° C. and depend on the method chosen. Reaction times are typically about 1 to about 18 hours.

Conversion of compounds of formula (9) to compounds of formula (10) can be accomplished by treatment of the former with N-hydroxyphthalimide, a trialkylphosphine or triarylphosphine, and a diazo compound. Representative trialkylphosphines include tributylphosphine and trimethylphosphine; representative triarylphosphines include triphenylphosphine and tri-o-tolylphosphine; and representative diazo compounds include DEAD and DIAD. Examples of solvents used in this reaction include THF, MTBE, diethyl ether, benzene, toluene, or mixtures thereof. The reaction temperatures are about 25° C. to about 35° C. Reaction times are typically about 4 to about 18 hours.

The conversion of compounds of formula (10) to compounds of formula (11) can be accomplished by treatment of the former with hydrazine. Examples of solvents used in this reaction include ethanol, methanol, water, dioxane, and mixtures thereof. The reaction temperatures are about 60° C. to about 120° C. Reaction times are typically about 15 minutes to about 1 hour.

Scheme 5

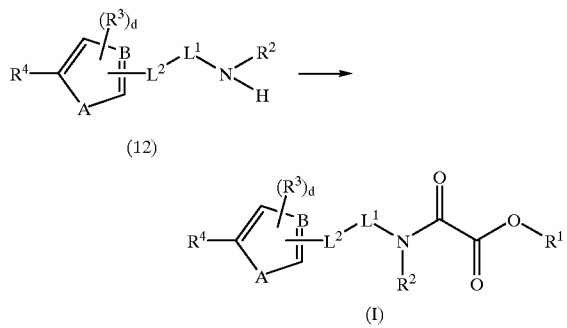

As shown in Scheme 5, compounds of formula (12) can be converted to compounds of formula (I) by treatment of the former with an alkyl oxalyl chloride and base. Representative bases include diisopropylethylamine, triethylamine, and pyridine. Examples of solvents include DME, dioxane, and DMF. The reaction temperatures are about −5° C. to about 25° C., and the reaction times are typically about 30 minutes to about 12 hours.

Intraconversion of compounds of formula (I) can be accomplished by hydrolysis with aqueous base followed by treatment with acid. Representative bases include sodium hydroxide, potassium hydroxide, and lithium hydroxide. Examples of acids include hydrochloric acid, sulfuric acid, and nitric acid. The reaction temperatures are about 25° C. to about 100° C. and the reaction times are typically about 1 to about 4 hours.

Scheme 6

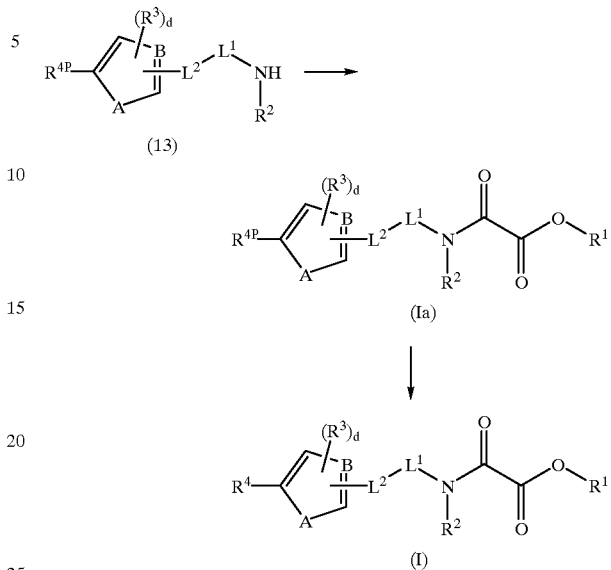

As shown in Scheme 6, compounds of formula (13) can be converted to compounds of formula (Ia) by the chemistry described for the conversion of compounds of formula (12) to compounds of formula (I) in Scheme 5. The conversion of the compounds of formula (Ia) to compounds of formula (I) can be accomplished by the chemistry described for the conversion of compounds of formula (1) to compounds of formula (2) in Scheme 1.

The invention will now be described in connection with other particularly preferred embodiments of Schemes 1–5, which are not intended to limit its scope. On the contrary, the invention covers all alternatives, modifications, and equivalents which are included within the scope of the claims. Thus, the following examples will illustrate an especially preferred practice of the invention, it being understood that the examples are for the purposes of illustration of certain preferred embodiments and are presented to provide what is believed to be the most useful and readily understood description of its procedures and conceptual aspects.

EXAMPLE 1

((2-(4-bromophenyl)-2-cyclohexylethyl)amino)(oxo) acetic Acid

EXAMPLE 1A (4-bromophenyl)(cyclohexyl)acetonitrile

A suspension of NaH (1.1 g, 27.5 mmol) in DMF (15 mL) and benzene (30 mL) at 0° C. was treated dropwise with 4-bromophenylacetonitrile (5.0 g, 25.5 mmol), stirred for 45 minutes, treated portionwise with cyclohexyl bromide (3.15 mL, 25.5 mmol), warmed to room temperature, stirred for 90 minutes, treated with water, and extracted with diethyl ether. The extract was washed with water and brine, dried ($Na_2SO_4$), filtered, and concentrated. The concentrate was purified by flash column chromatography on silica gel with 5:1 hexanes/ethyl acetate to provide the desired product.

EXAMPLE 1B 2-(4-bromophenyl)-2-cyclohexylethanamine

A solution of Example 1A (1.5 g, 5.4 mmol) in toluene (15 mL) at room temperature was treated dropwise with 1M DIBAL-H in toluene (5.4 mL, 5.4 mmol). After TLC showed complete consumption of the starting material, the concentrate was dissolved in THF (20 mL), treated with 1M $BH_3$·THF (11.0 mL, 11.0 mmol), stirred for 2 hours, treated dropwise with saturated $NH_4Cl$, stirred for 2 hours, and

EXAMPLE 1C

Ethyl ((2-(4-bromophenyl)-2-cyclohexylethyl)amino)-(oxo)acetate

The desired product was prepared by substituting Example 1B for Example 16B in Example 16C.

EXAMPLE 1D ((2-(4-bromophenyl)-2-cyclohexylethyl)amino)(oxo)acetic Acid

The desired product was prepared by substituting Example 1C for Example 16C in Example 16D. MS (ESI (+)) m/z 354 and 356 (M+H)$^+$; $^1$H NMR (300 MHz, DMSO-d$_6$) δ8.53 (t, 1H), 7.45 (d, 2H), 7.09 (d, 2H), 3.60–3.30 (m, 2H), 2.80–2.67 (m, 1H), 1.87–0.60 (m, 11H).

EXAMPLE 2

(benzyl(2-(4-bromophenyl)-2-cyclohexylethyl)amino)-(oxo)acetic Acid

The desired product was prepared by substituting Example 1A for Example 16A in Examples 16B–16D. MS (ESI(+)) m/z 444 and 446 (M+H)$^+$; $^1$H NMR (300 MHz, DMSO-d$_6$) δ7.55–7.47 (dd, 2H), 7.42–7.25 (m, 3H), 7.22 (dd, 1H), 7.12 (t, 3H), 4.35 (dd, 1H), 3.88 (dd, 1H), 3.77–3.21 (m, 2H), 2.90–2.70 (m, 1H), 1.78–0.53 (m, 11H).

EXAMPLE 3

(((4-bromophenyl)(cyclohexyl)methoxy)amino)(oxo)acetic Acid

EXAMPLE 3A 1-((amino)oxy)(cyclohexyl)methyl)-4-bromobenzene

The desired product was prepared by substituting 4-bromobenzaldehyde for 4-(2-quinolinyl)benzaldehyde in the procedure described in *Tetrahedron: Asymmetry* 1996, 7, 2645.

EXAMPLE 3B (((4-bromophenyl)(cyclohexyl)methoxy)amino)(oxo)acetic Acid

The desired product was prepared by substituting Example 3A for 2-(4-((amino)oxy)(cyclohexyl)methyl)phenyl)-quinoline in Example 4. MS (ESI(−)) m/z 354 (M−H)$^−$; $^1$H NMR (300 MHz, DMSO-d$_6$) δ7.52 (d, 2H), 7.26 (d, 2H), 4.65 (d, 1H), 1.98 (m, 1H), 1.69(m, 2H), 1.15–1.05 (m, 4H), 0.92 (m, 2H).

EXAMPLE 4

((cyclohexyl(3-(2-quinolinyl)phenyl)methoxy)amino)-(oxo)acetic Acid

EXAMPLE 4A

Ethyl ((cyclohexyl(3-(2-quinolinyl)phenyl)methoxy)amino)-(oxo)acetate

A mixture of 2-(4-((amino)oxy)(cyclohexyl)methyl)-phenyl)quinoline (119 mg, 0.32 mmol), prepared as described in *Tetrahedron: Asymmetry* 1996, 7, 2645), and diisopropylethylamine (0.112 mL, 0.64 mmol) in dichloromethane (2.0 mL) at 0° C. was treated with ethyl oxalyl chloride (72 μL, 0.65 mmol), stirred for 1 hour, treated with water, and extracted with ethyl acetate. The extract was dried (Na$_2$SO$_4$), filtered, and concentrated. The concentrate was purified by flash column chromatography on silica gel with 2:3 hexanes/ethyl acetate to provide the desired product. MS (ESI(+)) m/z 433 (M+H)$^+$; $^1$H NMR (300 MHz, DMSO-d$_6$) δ8.49 (d, 1H), 8.25–8.17 (m, 3H), 8.09 (d, 1H), 8.02 (d, 1H), 7.80 (dt, 1H), 7.61 (dt, 1H), 7.53 (t, 1H), 7.44 (d, 1H), 4.82 (d, 1H), 4.13 (q, 2H), 2.08 (m, 1H), 1.75 (m, 2H), 1.60 (m, 2H), 1.48–1.10 (m, 6H).

EXAMPLE 4B ((cyclohexyl(3-(2-quinolinyl)phenyl)methoxy)amino)-(oxo)acetic Acid A solution of Example 4A (70 mg, 0.162 mmol) in ethanol (2 mL) at room temperature was treated with 2M NaOH (1 mL), stirred for 2 hours, adjusted to pH 1 with 1M HCl, and extracted with ethyl acetate. The extract was dried (Na$_2$SO$_4$), filtered, and concentrated to provide the desired product. MS (ESI(+)) m/z 405 (M+H)$^+$; $^1$H NMR (300 MHz, DMSO-d$_6$) δ11.96 (br s, 1H), 8.49 (d, 1H), 8.23–8.17 (m, 3H), 8.06 (d, 1H), 8.02 (d, J=8.2 Hz, 1H), 7.80 (dt, 1H), 7.61 (dt, 1H), 7.53 (t, 1H), 7.43 (d, 1H), 4.82 (d, 1H), 2.08 (m, 1H), 1.82–1.70 (m, 2H), 1.60 (m, 2H), 1.48–1.10 (m, 6H).

EXAMPLE 5

(benzyl(2,3-dichloro-4-(1-naphthyl)benzyl)amino)(oxo)acetic Acid

EXAMPLE 5A 2,3-dichloro-4-formylphenyl Trifluoromethanesulfonate

A solution of 2,3-dichloro-4-hydroxybenzaldehyde (9.1 g, 48 mmol), prepared as described in *J. Med. Chem.* 1994, 19, 534), in pyridine (45 mL) at 0° C. was treated portionwise with trifluoromethanesulfonic anhydride (15.6 g, 0.055 mol), warmed to room temperature, stirred for 1 hour, and poured into a mixture of ice water, concentrated HCl, and diethyl ether. The organic phase was dried (Na$_2$SO$_4$), filtered, and concentrated. The concentrate was treated with warm heptane, filtered, and concentrated to provide the desired product.

EXAMPLE 5B 2,3-dichloro-4-(1-naphthyl)benzaldehyde

A mixture of Example 5A (0.20 g, 0.62 mmol), 1-naphthylboronic acid (0.13 g, 0.74 mmol), Pd(PPh$_3$)$_4$ (20 mg), and 2M Na$_2$CO$_3$ (0.62 mL) in toluene (2.0 mL) was heated to 100° C., stirred for 16 hours, and concentrated. The concentrate was purified by flash column chromatography on silica gel with hexanes to 5:1 hexanes/ethyl acetate to provide the desired product.

EXAMPLE 5C

N-benzyl(2,3-dichloro-4-(1-naphthyl)phenyl)methanamine

A solution of Example 5B (65 mg, 0.22 mmol) and benzylamine (0.024 mL, 0.22 mmol) in 1,2-dichloroethane (3 mL) at room temperature was treated with acetic acid (0.05 mL, 0.84 mmol), stirred for 2 hours, treated with sodium triacetoxyborohydride (64 mg, 0.31 mmol), stirred for 16 hours, and treated with saturated $NaHCO_3$. The organic layer was dried ($MgSO_4$), filtered, and concentrated. The concentrate was purified by flash column chromatography on silica gel with 2:1 hexanes/ethyl acetate to ethyl acetate to provide the desired product. MS (ESI(+)) m/z 393 $(M+H)^+$; $^1H$ NMR ($CDCl_3$, 300 MHz) δ7.92 (d, 2H), 7.56–7.46 (m, 3H), 7.45–7.26 (m, 9H), 4.05 (s, 2H), 3.93 (s, 2H).

EXAMPLE 5D

Ethyl (benzyl(2,3-dichloro-4-(1-naphthyl)benzyl) amino)-(oxo)acetate

A solution of Example 5C (0.035 mg, 0.089 mmol) and triethylamine (0.042 mL, 0.3 mmol) in dichloromethane (2 mL) at 0° C. was treated dropwise with ethyl oxalyl chloride, warmed to room temperature, stirred for 1 hour, and treated with water. The organic phase was dried ($MgSO_4$), filtered, and concentrated. The concentrate was purified by flash column chromatography on silica gel with 5:1 hexanes/ethyl acetate to provide the desired product.

MS (ESI(+)) 493 $(M+H)^+$.

EXAMPLE 5E (benzyl(2,3-dichloro-4-(1-naphthyl)benzyl)amino) (oxo)acetic Acid The desired product was prepared by substituting Example 5D for Example 16C in Example 16D. MS (DCI/$NH_3$) m/z 465 $(M+H)^+$; $^1H$ NMR (300 MHz, $CDCl_3$) δ8.02 (d, 2H), 7.65–7.48 (m, 4H), 7.45–7.30 (m, 5H), 7.30–7.20 (m, 3H), 4.60 (m, 4H).

EXAMPLE 6

N-benzyl-2-hydroxy-N-((4,1'-binaphth-1-yl)methyl) amino)-(oxo)acetic Acid

The desired product was prepared by substituting 4-hydroxy-1-naphthaldehyde for 2,3-dichloro-4-hydroxybenzaldehyde in Example 5. MS (ESI(+)) m/z 446 $(M+H)^+$; $^1H$ NMR (300 MHz, $CDCl_3$) δ7.98–7.88 (m, 2H), 7.50–7.45 (m, 1H), 7.42–7.26 (m, 4H), 7.30–7.20 (m, 4H), 7.20–7.10 (m, 7H), 5.17 (d, 2H), 4.65 (d, 2H).

EXAMPLE 7

(benzyl(2-chloro-4-(1-naphthyl)benzyl)amino)(oxo) acetic Acid

The desired product was prepared by substituting 2-chloro-4-hydroxybenzaldehyde for 2,3-dichloro-4-hydroxybenzaldehyde in Example 5. MS (ESI(+)) m/z 430 $(M+H)^+$; $^1H$ NMR (300 MHz, $CDCl_3$) δ7.82–7.70 (m, 3H), 7.50–7.04 (m, 12H), 4.64 (d, 2H), 4.49 (d, 2H).

EXAMPLE 8

(benzyl((4-bromo-5-(1-naphthyl)-2-thienyl)methyl) amino)-(oxo)acetic Acid

The desired product was prepared by substituting 4,5-dibromo-2-thiophenecarbaldehyde for Example 5A in Examples 5B–5E. MS (ESI(+)) m/z 481 $(M+H)^+$; $^1H$ NMR (300 MHz, $CDCl_3$)δ7.84–7.78 (m, 2H), 7.62 (t, 1H), 7.45–7.32 (m, 4H), 7.25–7.05 (m, 5H), 6.75 (d, 1H), 4.50 (s, 2H), 4.34 (d, 2H).

EXAMPLE 9

(benzyl((5-(1-naphthyl)-2-thienyl)methyl)amino) (oxo)acetic Acid

The desired product was prepared by substituting 5-bromo-2-thiophenecarbaldehyde for Example 5A in Examples 5B–5E. MS (ESI(+)) m/z 402 $(M+H)^+$; $^1H$ NMR (300 MHz, $CDCl_3$) δ8.07 (t, 1H), 7.77 (d, 1H), 7.69 (d, 1H), 7.40–7.00 (m, 9H), 6.87 (dd, 1H), 6.78 (dd, 1H), 4.55 (d, 2H), 4.40 (s, 2H).

EXAMPLE 10

(benzyl(4-(2-quinolinylmethoxy)benzyl)amino)(oxo) acetic Acid

The desired product was prepared by substituting 4-(2-quinolinylmethoxy)-benzaldehyde, prepared as described in J Med. Chem. 2000, 43, 690, for Example 5B in Examples 5C–5E. MS (ESI(+)) m/z 427 $(M+H^+$; $^1H$ NMR (300 MHz, $CDCl_3$) δ8.42–8.30 (m, 2H), 7.94–7.78 (m, 3H), 7.66 (dd, 1H), 7.40–7.26 (m, 3H), 7.28–7.10 (m, 4H), 6.98 (dd, 2H), 5.52 (s, 2H), 4.65 (d, 2H), 4.46 (d, 2H).

EXAMPLE 11 oxo((2-phenylethyl)(4-(2-quinolinylmethoxy)benzyl) amino)-acetic Acid

The desired product was prepared by substituting 4-(2-quinolinylmethoxy)benzaldehyde (prepared as described in J Med. Chem. 2000, 43, 690) and phenylethanamine for Example 5B and benzylamine, respectively, in Examples 5C–5E. MS (ESI(+)) m/z 441 $(M+H)^+$; $^1H$ NMR (300 MHz, DMSO-$d_6$) δ8.40 (d, 1H), 8.00 (t, 2H), 7.80–7.75 (m, 1H), 7.68–7.58 (m, 2H), 7.40 (d, 1H), 7.28–7.08 (m, 6H), 7.02 (dd, 2H), 5.34 (s, 2H), 4.35 (s, 1H), 4.04 (br s, 1H), 3.20–3.10 (m, 2H), 2.85–2.75 (m, 1H), 2.60–2.50 (m, 1H).

EXAMPLE 12

(cyclohexyl(4-(2-quinolinylmethoxy)benzyl)amino) (oxo)acetic Acid

The desired product was prepared by substituting 4-(2-quinolinylmethoxy)benzaldehyde (prepared according to the procedure described in J Med. Chem. 2000, 43, 690) and cyclohexylamine for Example 5B and benzylamine, respectively, in Examples 5C–5E. MS (ESI(+)) m/z 419 $(M+H)^+$; $^1H$ NMR (300 MHz, DMSO-$d_6$) δ8.42 (d, 1H), 8.0 (t, 2H), 7.79 (td, 1H), 7.68 (d, 1H), 7.62 (t, 1H), 7.30 (d, 1H), 7.19 (d, 1H), 7.06 (d, 1H), 7.02 (d, 1H), 5.34 (s, 1H), 4.42 (d, 1H), 3.90–3.74 (m, 1H), 1.75–1.33 (m, 6H), 1.24–0.87 (m, 4H).

EXAMPLE 13

(benzyl(2-methoxy-4-(1-naphthyl)benzyl)amino) (oxo)acetic Acid

The desired product was prepared by substituting 4-hydroxy-2-methoxybenzaldehyde for 2,3-dichloro-4-hydroxybenzaldehyde in Example 5. MS (ESI(+)) m/z 426 $(M+H)^+$; $^1H$ NMR (300 MHz, DMSO-$d_6$) δ7.98 (dd, 1H), 7.83 (dd, 1H), 7.66–7.17 (m, 10H), 7.04 (d, 2H), 4.53 (s, 2H), 4.50 (s, 1H), 4.39 (s, 1H), 3.78 (s, 3H).

EXAMPLE 14

((2-hydroxyethyl)((4,1'-binaphth-1-yl)methyl)amino)-(oxo)acetic Acid

The desired product was prepared by substituting 2-aminoethanol and 4-hydroxy-1-naphthaldehyde for benzylamine and 2,3-dichloro-4-hydroxybenzaldehyde in Example 5. MS (ESI(+)) m/z 400 (M+H)$^+$; $^1$H NMR (300 MHz, CDCl$_3$) δ8.12 (d, 1H), 7.96 (dd, 2H), 7.62–7.46 (m, 7H), 7.38–7.27 (m, 3H), 5.30 (dd, 2H), 4.43 (t, 2H), 3.58–3.54 (m, 2H).

EXAMPLE 15

((2-cyclohexyl-2-(4-(1-naphthyl)phenyl)ethyl)(2-(4-morpholinyl)ethyl)amino)(oxo)acetic Acid The desired product was prepared by substituting 2-(4-morpholinyl)ethanamine for benzylamine in Example 16.

MS (ESI(+)) m/z 515 (M+H)$^+$; $^1$H NMR (300 MHz, DMSO-d$_6$) δ7.98 (dd, 2H), 7.83 (t, 1H), 7.61–7.28 (m, 8H), 4.03–2.76 (m, 15H), 2.00–0.70 (m, 11H).

EXAMPLE 16

(benzyl(2-cyclohexyl-2-(4-(1-naphthyl)phenyl)ethyl)amino)-(oxo)acetic Acid

EXAMPLE 16A cyclohexyl(4-(1-naphthyl)phenyl)acetonitrile

A mixture of Example 1A (3.0 g, 10.8 mmol), 1-naphthylboronic acid (2.04 g, 11.9 mmol), Pd(PPh$_3$)$_4$ (249 mg, 0.22 mmol), and 3M Na$_2$CO$_3$ (9.0 mL, 27 mmol) in toluene (18 mL) was heated to 100° C. in a sealed tube, stirred for 14 hours, cooled to room temperature, and partitioned between water and diethyl ether. The organic phase was washed with brine, dried (Na$_2$SO$_4$), filtered, and concentrated. The concentrate was purified by flash column chromatography on silica gel with 20:1 to 10:1 hexanes/ethyl acetate to provide the desired product.

EXAMPLE 16B

N-benzyl-2-cyclohexyl-2-(4-(1-naphthyl)phenyl)ethanamine

A solution of Example 16A (1.0 g, 3.07 mmol) in toluene at room temperature was treated dropwise with 1.5M DIBAL-H in toluene (2.25 mL, 3.41 mmol), stirred for 30 minutes, quenched slowly with 3M HCl, and extracted with diethyl ether. The extract was washed with brine, dried (Na$_2$SO$_4$), filtered, and concentrated to provide cyclohexyl (4-(1-naphthyl)phenyl)acetaldehyde.

The concentrate was dissolved in 2:1 methanol/THF, treated with benzylamine (0.37 mL, 3.40 mmol), stirred for 4 hours, treated with NaBH$_4$ (0.12 g, 3.40 mmol), stirred for 1 hour, poured into saturated NaHCO$_3$, and extracted with dichloromethane. The extract was washed with brine, dried (Na$_2$SO$_4$), filtered, and concentrate to provide the desired product of sufficient purity for subsequent use.

EXAMPLE 16C

Ethyl (benzyl(2-cyclohexyl-2-(4-(1-naphthyl)phenyl)ethyl)-amino)(oxo)acetate

A mixture of Example 16B (75.0 mg, 0.18 mmol) and diisopropylamine (100 μL, 0.36 mmol) in dichloromethane (2 mL) at 0° C. was treated with ethyl oxalyl chloride (36 mL, 0.32 mmol), stirred for 1 hour, treated with water, and extracted with ethyl acetate. The extract was dried (Na$_2$SO$_4$), filtered, and concentrated. The concentrate was purified by flash column chromatography on silica gel with 5:1 hexanes/ethyl acetate to provide the desired product.

EXAMPLE 16D (benzyl(2-cyclohexyl-2-(4-(1-naphthyl)phenyl)ethyl)amino)-(oxo)acetic Acid A solution of Example 16C (50.0 mg, 0.096 mmol) in ethanol (2 mL) at room temperature was treated with 2M NaOH (0.2 mL), stirred for 2 hours, adjusted to pH 1 with 1M HCl, and extracted with ethyl acetate. The extract was dried (Na$_2$SO$_4$), filtered, and concentrated to provide the desired product. MS (ESI(+)) m/z 492 (M+H)$^+$; $^1$H NMR (300 MHz, DMSO-d$_6$) δ8.04–7.83 (m, 2H), 7.67–7.00 (m, 14H), 4.54–4.33 (m, 1H), 3.93–3.62 (m, 1H), 3.00–2.70 (m, 1H), 1.83–0.67 (m, 11H).

EXAMPLE 17

((2-cyclohexyl-2-(4-(1-naphthyl)phenyl)ethyl)(2-phenylethyl)amino)(oxo)acetic Acid The desired product was prepared by substituting phenylethanamine for benzylamine in Example 16.

MS (ESI(+)) m/z 506 (M+H)$^+$; $^1$H NMR (300 MHz, DMSO-d$_6$) δ7.96 (dd, 2H), 7.73 (dd, 1H), 7.62–7.46 (m, 2H), 7.46–7.30 (m, 5H), 7.30–7.00 (m, 6H), 4.10–3.89 (m, 1H), 3.54–3.10 (m, 2H), 2.97–2.25 (m, 4H), 2.00–0.70 (m, 11H).

EXAMPLE 18

((2-cyclohexyl-2-(4-(1-naphthyl)phenyl)ethyl)(2-(3,4-dimethoxyphenyl)ethyl)amino)(oxo)acetic Acid The desired product was prepared by substituting 2-(3,4-dimethoxy-phenyl)ethanamine for benzylamine in Example 16. MS (ESI(+)) m/z 566 (M+H)$^+$; $^1$H NMR (300 MHz, DMSO-d$_6$) δ7.96 (dd, 2H), 7.71 (m, 1H), 7.67–7.47 (m, 5H), 7.43–7.30 (m, 3H), 6.79 (dd, 1H), 6.67 (dd, 1H), 6.60–6.53 (m, 1H), 4.01–3.85 (m, 1H), 3.68 (s, 3H), 3.64 (s, 3H), 3.50–3.10 (m, 2H), 2.94–2.47 (m, 4H), 2.00–0.70 (m, 11H).

EXAMPLE 19

(benzyl(2-(carboxymethoxy)-4-(1-naphthyl)benzyl)amino)-(oxo)acetic Acid

A room temperature solution of Example 20E in 1:1 TFA/dichloromethane was stirred for 2 hours and concentrated to provide the desired product. MS (ESI(+)) m/z 470 (M+H)$^+$; $^1$H NMR (300 MHz, DMSO-d$_6$) δ8.01–7.83 (m, 3H), 7.60–7.20 (m, 10H), 6.96 (d, 1H), 6.81 (d, 1H), 4.51 (d, 1H), 4.44 (s, 1H), 4.31 (s, 1H), 4.27 (s, 2H).

EXAMPLE 20

(benzyl(2-(2-tert-butoxy-2-oxoethoxy)-4-(1-naphthyl)benzyl)amino)(oxo)acetic Acid

EXAMPLE 20A

N-benzyl(2-methoxy-4-(1-naphthyl)phenyl)methanamine

The desired product was prepared by substituting 4-hydroxy-2-methoxybenzaldehyde for 2,3-dichloro-4-hydroxybenzaldehyde in Examples 5A–5C.

EXAMPLE 20B 2-((benzylamino)methyl)-5-(1-naphthyl)phenol

A solution of Example 20A (1.75 g, 4.95 mmol) in dichloromethane (40 mL) at −78° C. was treated with 1M BBr$_3$ in dichloromethane (15.0 mL, 15.0 mmol), warmed to room temperature, stirred for 5 hours, quenched with water, and extracted with dichloromethane. The extract was washed with saturated NaHCO$_3$ and brine, dried (Na$_2$SO$_4$), filtered, and concentrated to provide the desired product of sufficient purity for subsequent use.

EXAMPLE 20C

Ethyl (benzyl(2-hydroxy-4-(1-naphthyl)benzyl) amino)-(oxo)acetate

The desired product was prepared by substituting Example 20B for Example 5C in Example 5D.

EXAMPLE 20D

Ethyl (benzyl(2-(2-tert-butoxy-2-oxoethoxy)-4-(1-naphthyl)benzyl)amino)(oxo)acetate A solution of Example 20C (300 mg, 0.68 mmol) in DMF (5.0 mL) was treated with K$_2$CO$_3$ (189 mg, 1.36 mmol) and t-butyl bromoacetate (121 μL, 0.82 mmol), heated at 75° C. for 1.5 hours, quenched with water, and extracted with ethyl acetate. The extract was washed with brine, dried (Na$_2$SO$_4$), filtered, and concentrated. The concentrate was purified by flash column chromatography on silica gel 4:1 hexanes/ethyl acetate to provide the desired product.

EXAMPLE 20E (benzyl(2-(2-tert-butoxy-2-oxoethoxy)-4-(1-naphthyl)benzyl)amino)(oxo)acetic Acid The desired product was prepared by substituting Example 20D for Example 16C in Example 16D. MS (ESI(+)) m/z 526 (M+H)$^+$.

EXAMPLE 21

3-(((2-((benzyl(carboxycarbonyl)amino)methyl)-5-(1-naphthyl)phenoxy)acetyl)amino)benzoic Acid

EXAMPLE 21A (2-((benzyl(ethoxy(oxo)acetyl)amino)methyl)-5-(1-naphthyl)phenoxy)acetic Acid A room temperature solution of Example 20D (300 mg, 0.54 mmol) in 1:1 TFA/dichloromethane was stirred for 2 hours and concentrated to provide the desired product.

EXAMPLE 21B

Methyl 3-(((2-((benzyl(ethoxy(oxo)acetyl)amino) methyl)-5-(1-naphthyl)phenoxy)acetyl)amino) benzoate A room temperature solution of Example 21A (50 mg, 0.10 mmol) in DMF (1.0 mL) was treated with ethyl 3-aminobenzoate (20 μL, 0.13 mmol), HOBT (23 mg, 0.14 mmol), EDCI (29 mg, 0.15 mmol), and Et$_3$N (21 μL, 0.15 mmol), stirred for 5 hours, and partitioned between ethyl acetate and water. The organic phase was washed with brine, dried (Na$_2$SO$_4$), filtered, and concentrated. The concentrate was purified by flash column chromatography on silica gel with 2:5 hexanes/ethyl acetate to provide the desired product.

EXAMPLE 21C 3-(((2-((benzyl(carboxycarbonyl)amino)methyl)-5-(1-naphthyl)phenoxy)acetyl)amino)benzoic Acid The desired product was prepared by substituting Example 21B for Example 16C in Example 16D. MS (ESI(+)) m/z 589 (M+H)$^+$; $^1$H NMR (300 MHz, DMSO-d$_6$) δ8.37 (s, 2H), 8.02–7.61 (m, 5H), 7.61–7.13 (m, 8H), 7.10–6.90 (m, 4H), 4.76–4.46 (m, 2H), 4.43 (d, 2H), 4.03 (s, 2H).

EXAMPLE 22

(benzyl(2-(2-(((4-(methoxycarbonyl)cyclohexyl) methyl)amino)-2-oxoethoxy)-4-(1-naphthyl)benzyl) amino)(oxo)acetic Acid The desired product was prepared by substituting methyl trans-4-(aminomethyl)cyclohexanecarboxylate for ethyl 3-aminobenzoate in Example 21. MS (ESI(+)) m/z 623 (M+H)$^+$;

$^H$ $^1$NMR (300 MHz, DMSO-d$_6$) δ8.16 (s, 1H), 7.97 (dd, 2H), 7.83 (d, 1H), 7.76 (d, 1H) 7.60–7.07 (m, 8H), 7.04 (t, 1H), 6.94 (d, 1H), 6.79 (s, 1H), 4.57 (d, 2H), 4.48 (d, 2H), 4.38 (d, 2H), 3.58 (s, 3H), 2.96 (t, 1H), 1.83–1.57 (m, 4H), 1.50–1.04 (m, 4H), 0.94–0.74 (m, 1H).

EXAMPLE 23

(benzyl(4-(1-naphthyl)-2-(2-oxo-2-((3-(2-oxo-1-pyrrolidinyl)propyl)amino)ethoxy)benzyl)amino) (oxo)acetic Acid The desired product was prepared by substituting 1-(3-aminopropyl)-2-pyrrolidinone for ethyl 3-aminobenzoate in Example 21. MS (DCI/NH$_3$) m/z 594 (M+H)$^+$.

EXAMPLE 24

5-((2-((benzyl(carboxycarbonyl)amino)methyl)-5-(1-naphthyl)phenoxy)methyl)-2-furoic Acid The desired product was prepared by substituting ethyl 5-(chloromethyl)-2-furoate for tert-butyl bromoacetate in Example 20. MS (DCI/NH$_3$) m/z 536 (M+H)$^+$; $^1$H NMR (300 MHz, DMSO-d$_6$) δ7.99 (dd, 2H), 7.79 (m, 1H), 7.65–7.16 (m, 2H), 7.09 (m, 1H), 6.68 (dd, 1H), 5.23 (s, 2H), 4.53 (s, 2H), 4.50 (s, 1H), 4.40 (s, 1H).

EXAMPLE 25

((cyclohexyl(4-(2-quinolinylmethoxy)phenyl) methyl)amino)(oxo)acetic Acid

EXAMPLE 25A cyclohexyl(4-(2-quinolinylmethoxy)phenyl) methanamine

The desired product was prepared by substituting 4-(2-quinolinylmethoxy)benzaldehyde (prepared according to the procedure described in *J Med. Chem.* 2000, 43, 690) and phthalimide for 4-(2-quinolinyl)benzaldehyde and N-hydroxyphthalimide, respectively, in the procedure described in *Tetrahedron: Asymmetry* 1996, 7, 2645.

EXAMPLE 25B ((cyclohexyl(4-(2-quinolinylmethoxy)phenyl)methyl)amino)-(oxo)acetic Acid The desired product was prepared by substituting Example 25A for 2-(4-((amino)oxy)(cyclohexyl)methyl)phenyl)quinoline in Examples 4A and 4B. MS (DCI/NH$_3$) m/z 419 (M+H$^+$; $^1$H NMR (300 MHz, DMSO-d$_6$) δ8.49 (s, 1H), 8.41 (d, 1H), 8.01 (t, 2H), 7.79 (td, 1H), 7.67 (d, 1H), 7.62 (td, 1H), 7.23 (d, 2H), 6.99 (d, 2H), 5.33 (s, 2H), 4.38 (t, 1H), 1.87–1.50 (m, 5H), 1.30–0.70 (m, 6H).

EXAMPLE 26

((2-methoxy-4-(1-naphthyl)benzyl)(2-phenylethyl)amino)-(oxo)acetic Acid

The desired product was prepared by substituting 4-hydroxy-2-methoxybenzaldehyde and phenylethanamine for 2,3-dichloro-4-hydroxybenzaldehyde and benzylamine, respectively, in Example 5. MS (DCI/NH$_3$) m/z 440(M+H)$^+$; $^1$H NMR (300 MHz, DMSO-d$_6$) δ7.97 (dd, 2H), 7.87 (dd, 1H), 7.64–7.43 (m, 4H), 7.36–7.10 (m, 6H), 7.10–6.97 (m, 2H), 4.47 (d, 2H), 3.86 (s, 3H), 3.42 (m, 2H), 2.92 (m, 1H), 2.72 (m, 1H).

EXAMPLE 27

((2,3-dichloro-4-(1-naphthyl)benzyl)(2-phenylethyl)amino)-(oxo)acetic Acid

The desired product was prepared by substituting phenylethanamine for benzylamine in Example 5. MS (ESI(+)) m/z 479 (M+H)$^+$; $^1$H NMR (300 MHz, DMSO-d$_6$) δ8.02 (d, 2H), 7.64–7.52 (m, 2H), 7.50–7.40 (m, 4H), 7.35–7.20 (m, 6H), 4.68–4.62 (m, 1H), 4.40–4.00 (m, 1H), 3.62–3.52 (m, 2H), 3.00–2.82 (m, 2H).

EXAMPLE 28

((2-(4-(((carboxycarbonyl)amino)sulfonyl)phenyl)ethyl)(2-cyclohexyl-2-(4-(1-naphthyl)phenyl)ethyl)amino)(oxo)acetic Acid The desired product was prepared by substituting 4-(2-aminoethyl)benzenesulfonamide for benzylamine in Example 16.

MS (DCI/NH$_3$) m/z 657 (M+H)$^+$; $^1$H NMR (300 MHz, DMSO-d$_6$) δ7.94 (dd, 2H), 7.74 (d, 1H), 7.67 (dd, 2H), 7.61–7.48 (m, 2H), 7.44–7.32 (m, 4H), 7.09 (dd, 1H), 4.01 (dd, 1H), 3.51–2.60 (m, 10H), 2.00–0.70 (m, 13H).

EXAMPLE 29

((2-cyclohexyl-2-(4-(1-naphthyl)phenyl)ethyl)(3-(2-oxo-1-pyrrolidinyl)propyl)amino)(oxo)acetic Acid The desired product was prepared by substituting 1-(3-aminopropyl)-2-pyrrolidinone for benzylamine in Example 16.

MS (DCI/NH$_3$) m/z 527 (M+H)$^+$; $^1$H NMR (300 MHz, DMSO-d$_6$) δ8.00 (dd, 1H), 7.94 (d, 1H), 7.86–7.79 (m, 1H), 7.67–7.28 (m, 8H), 3.94 (td, 1H), 3.45–3.18 (m, 4H), 3.08–2.09 (m, 4H), 2.13 (t, 2H), 1.96–0.70 (m, 15H).

EXAMPLE 30

(benzyl((5-(1-naphthyl)(1,1'-biphenyl)-2-yl)methyl)amino)(oxo)acetic Acid

EXAMPLE 30A 2-((benzylamino)methyl)-5-(1-naphthyl)phenyl Trifluoromethanesulfonate The desired product was prepared by substituting Example 20B for 2,3-dichloro-4-hydroxybenzaldehyde in Example 5A.

EXAMPLE 30B

N-benzyl(5-(1-naphthyl)(1,1'-biphenyl)-2-yl)methanamine

The desired product was prepared by substituting Example 30A and phenylboronic acid for Example 5A and 1-naphthylboronic acid in Example 5B.

EXAMPLE 30C (benzyl((5-(1-naphthyl)(1,1'-biphenyl)-2-yl)methyl)amino)(oxo)acetic Acid The desired product was prepared by substituting Example 30B for Example 16B in Examples 16C and 16D. MS (DCI/NH$_3$) m/z 472 (M+H)$^+$; $^1$H NMR (300 MHz, DMSO-d$_6$) δ8.04–7.87 (m, 3H), 7.63–7.44 (m, 7H), 7.41–7.24 (m, 8H), 7.14 (d, 1H), 6.92 (m, 1H), 4.38 (s, 1H), 4.26 (s, 2H), 4.16 (s, 1H).

EXAMPLE 31

(benzyl((4'-formyl-5-(1-naphthyl)(1,1'-biphenyl)-2-yl)methyl)amino)(oxo)acetic Acid The desired product was prepared by substituting 4-formylphenylboronic acid for phenylboronic acid in Example 30. MS (DCI/NH$_3$) m/z 500 (M+H)$^+$; $^1$H NMR (300 MHz, DMSO-d$_6$) δ10.03 (d, 1H), 8.05–7.84 (m, 3H), 7.63–7.46 (m, 4H), 7.32 (dd, 1H), 7.20–7.09 (m, 3H), 6.91 (dd, 1H), 4.41 (s, 1H), 4.30 (d, 1H), 4.20 (s, 1H).

EXAMPLE 32

(benzyl(2-((1E)-3-tert-butoxy-3-oxo-1-propenyl)-4-(1-naphthyl)benzyl)amino)(oxo)acetic Acid

EXAMPLE 32A

Tert-Butyl (2E)-3-(2-((benzylamino)methyl)-5-(1-naphthyl)phenyl)-2-propenoate

The desired product was prepared by substituting Example 30A for Example 34A in Example 34B.

EXAMPLE 32B

Tert-Butyl (2E)-3-(2-((benzyl(ethoxy(oxo)-acetyl)amino)methyl)-5-(1-naphthyl)phenyl)-2-propenoate The desired product was prepared by substituting Example 32A for Example 16B in Example 16C.

EXAMPLE 32C (benzyl(2-((1E)-3-tert-butoxy-3-oxo-1-propenyl)-4-(1-naphthyl)benzyl)amino)(oxo)acetic Acid The desired product was prepared by substituting Example 32B for Example 16C in Example 16D. MS (DCI/NH$_3$) m/z 539 (M+NH$_4$)$^+$; $^1$H NMR (300 MHz, DMSO-d$_6$) δ7.99 (dd, 1H), 7.81–7.45 (m, 10H), 7.39–7.25 (m, 4H), 7.19 (dd, 1H), 6.39 & 6.37 (2d, 1H total), 4.68 (s, 1H), 4.60 (s, 1H), 4.48 (s, 1H), 4.45 (s, 1H), 1.45 (s, 9H).

EXAMPLE 33

(2E)-3-(2-((benzyl(carboxycarbonyl)amino)methyl)-5-(1-naphthyl)phenyl)-2-propenoic Acid The desired product was prepared by substituting Example 32C for Example 20E in Example 19. MS (DCI/

NH$_3$) m/z 483 (M+NH$_4$)$^+$; $^1$H NMR (300 MHz, DMSO-d$_6$) δ8.02 (dd, 1H), 7.97 (d, 1H), 7.87–7.77 (m, 1H), 7.74–7.52 (m, 8H), 7.37–7.23 (m, 3H), 7.18 (dd, 1H), 6.39 & 6.30 (2d, 1H total), 4.60 (s, 1H), 4.46 (s, 1H), 4.42 (s, 1H), 4.33 (s, 1H).

EXAMPLE 34

(benzyl(2-(4-((1E)-3-tert-butoxy-3-oxo-1-propenyl) phenyl)-2-cyclohexylethyl)amino)(oxo)acetic Acid

EXAMPLE 34A

Ethyl (benzyl(2-(4-bromophenyl)-2-cyclohexylethyl)amino)-(oxo)acetate

The desired product was prepared by substituting Example 1A for Example 16A in Examples 16B and 16C.

EXAMPLE 34B

Tert-Butyl (2E)-3-(4-(2-(benzyl(ethoxy(oxo)acetyl) amino)-1-cyclohexylethyl)phenyl)-2-propenoate A solution of Example 34A (200 mg, 0.32 mmol) in DMF (3.0 mL) at room temperature was treated with Pd (OAc)$_2$ (0.013 mmol) and P(o-tolyl)$_3$ (8 mg, 0.026 mmol), flushed with nitrogen, treated with tert-butyl acrylate (0.091 mL, 0.48 mmol) and triethylamine (0.012 mL, 0.64 mmol), heated at 90° C., stirred for 16 hours, and partitioned between ethyl acetate and water. The organic phase was washed with brine, dried (Na$_2$SO$_4$), filtered, and concentrated. The concentrate was purified by flash column chromatography on silica gel with 3:1 hexanes/ethyl acetate to provide the desired product.

EXAMPLE 34C (benzyl(2-(4-((1E)-3-tert-butoxy-3-oxo-1-propenyl) phenyl)-2-cyclohexylethyl)amino)(oxo)acetic Acid The desired product was prepared by substituting Example 34B for Example 20D in Example 20E. MS (DCI/NH$_3$) m/z 509 (M+NH$_4$)$^+$; $^1$H NMR (300 MHz, DMSO-d$_6$) δ7.63 (dd, 1H), 7.54 (d, 1H), 7.40–7.17 (m, 1H), 7.09 (d, 1H), 6.51 (d, 1H), 4.44 (d, 1H), 4.27 (d, 1H), 4.06 (s, 2H), 3.80–3.69 (m, 1H), 1.80–0.57 (m, 1H), 1.48 (s, 9H).

EXAMPLE 35

((2,3-dichloro-4-(1-naphthyl)benzyl)(2-(1,3-dioxo-1, 3-dihydro-2H-isoindol-2-yl)ethyl)amino)(oxo)acetic Acid The desired product was prepared by substituting 2-(2-aminoethyl)-1H-isoindole-1,3(2H)-dione for benzylamine in Example 5. MS (ESI(+)) m/z 548 (M+H)$^+$; $^1$H NMR (300 MHz, CDCl$_3$) δ7.90–7.80 (m, 3H), 7.80–7.70 (m, 2H), 7.56–7.25 (m, 3H), 7.55–7.46 (m, 3H), 7.42–7.36 (m, 2H), 4.33 (s, 2H), 4.04 (t, 2H), 3.27 (t, 2H).

EXAMPLE 36

(((1,1'-biphenyl)-4-yl(cyclohexyl)methoxy)amino) (oxo)acetic Acid

EXAMPLE 36A 4-((amino)oxy)(cyclohexyl)methyl)-1,1'-biphenyl

The desired product was prepared by substituting (1,1'-biphenyl)-4-carbaldehyde for 4-(2-quinolinyl)benzaldehyde in the procedure described in *Tetrahedron: Asymmetry* 1996, 7, 2645.

EXAMPLE 36B (((1,1'-biphenyl)-4-yl(cyclohexyl)methoxy)amino) (oxo)acetic Acid The desired product was prepared by substituting Example 36A for 2-(4-((amino)oxy)(cyclohexyl)methyl) phenyl)-quinoline in Example 4. MS (ESI(–)) m/z 352 (M–H)$^-$;

$^1$H NMR (300 MHz, DMSO-d$_6$) δ11.85 (br s, 1H), 7.7–7.6 (m, 4H), 7.51–7.42 (m, 2H), 7.40–7.34 (m, 3H), 4.72 (d, 1H), 2.03 (m, 1H), 1.72 (m, 2H), 1.58 (m, 2H), 1.33 (m, 1H), 1.15–1.05 (m, 4H), 0.92 (m, 1H).

EXAMPLE 37

(benzyl(4-(1-naphthyl)-2-((1E)-3-oxo-3-((3-(2-oxo-1-pyrrolidinyl)propyl)amino)-1-propenyl)benzyl) amino)-(oxo)acetic Acid

EXAMPLE 37A (2E)-3-(2-((benzyl(ethoxy(oxo)acetyl)amino) methyl)-5-(1-naphthyl)phenyl)-2-propenoic Acid The desired product was prepared by substituting Example 32B for Example 20D in Example 21A.

EXAMPLE 37B

Ethyl (benzyl(4-(1-naphthyl)-2-((1E)-3-oxo-3-((3-(2-oxo-1-pyrrolidinyl)propyl)amino)-1-propenyl) benzyl)amino)-(oxo)acetate The desired product was prepared by substituting Example 37A and 1-(3-aminopropyl)-2-pyrrolidinone for Example 21A and ethyl 3-aminobenzoate in Example 21B.

EXAMPLE 37C (benzyl(4-(1-naphthyl)-2-((1E)-3-oxo-3-((3-(2-oxo-1-pyrrolidinyl)propyl)amino)-1-propenyl)benzyl) amino)-(oxo)acetic Acid The desired product was prepared by substituting Example 37B for Example 16C in Example 16D.

MS (ESI(+)) m/z 590 (M+H$^+$; $^1$H NMR (300 MHz, CDCl$_3$) δ8.03 (dd, 1H), 7.99 (d, 1H), 7.85–7.26 (m, 13H), 7.22 (d, 1H), 6.56 (d, 1H), 4.71 (s, 1H), 4.62 (s, 1H), 4.55 (s, 1H), 4.52 (s, 1H), 3.18 (t, 2H), 3.11 (q, 2H), 2.19 (t, 2H), 1.90 (pent, 2H), 1.62 (pent, 2H)

EXAMPLE 38

(2E)-3-(4-(2-(benzyl(carboxycarbonyl)amino)-1-cyclohexylethyl)phenyl)-2-propenoic Acid The desired product was prepared by substituting Example 34C for Example 20E in Example 19. MS (ESI(+)) m/z 436 (M+H)$^+$; $^1$H NMR (300 MHz, DMSO-d$_6$) δ7.62 (dd, 1H), 7.58 (d, 1H), 7.40–7.16 (m, 7H), 7.09 (d, 1H), 6.51 (d, 1H), 4.42 (d, 1H), 4.27 (d, 1H), 3.83 (d, 1H), 3.78–3.53 (m, 1H), 2.91–2.75 (m, 1H), 1.79–0.54 (m, 11H).

EXAMPLE 39

(benzyl(2-cyclohexyl-2-(4-((1E)-3-(4-hydroxy-3,5-diphenylanilino)-3-oxo-1-propenyl)phenyl)ethyl) amino)-(oxo)acetic Acid The desired product was prepared by substituting Example 34B and 3,5-diphenyl-4-hydroxyaniline for Example 20D and ethyl 3-aminobenzoate, respectively, in Example 21.

MS (ESI(+)) m/z 679 (M+H)+; 1H NMR (300 MHz, DMSO-d6) δ10.16 (s, 1H), 8.17 (s, 1H), 7.64–7.18 (m, 21H), 7.10 (d, 1H), 6.79 (d, 1H), 4.44 (d, 1H), 4.28 (d, 1H), 3.84 (d, 1H), 3.78–3.56 (m, 1H), 2.93–2.75 (m, 1H), 1.80–0.58 (m, 11H).

EXAMPLE 40

(benzyl(2-cyclohexyl-2-(4-(3-(4-hydroxy-3,5-diphenylanilino)-3-oxopropyl)phenyl}ethyl)amino)(oxo)acetic Acid A mixture of Example 39 (34.0 mg, 0.050 mmol) and 10% Pd/C (5.0 mg) in ethanol (2.0 mL) at room temperature was stirred under hydrogen for 16 hours, filtered through diatomaceous earth (Celite®) with ethanol rinsing, and concentrated to provide the desired product.

MS (DCI/NH3) m/z 681 (M+H)+; 1H NMR (300 MHz, DMSO-d6) δ9.82 (d, 1H), 8.07 (d, 1H), 7.55–6.96 (m, 21H), 4.44 (d, 1H), 4.22 (d, 1H), 3.80–3.70 (m, 1H), 3.65 (d, 1H), 3.47 (d, 1H), 2.90 (t, 1H), 2.61 (t, 2H), 1.78–0.53 (m, 11H).

EXAMPLE 41

((2-(1-(tert-butoxycarbonyl)-4-piperidinyl)-2-(4-(1-naphthyl)phenyl)ethyl)(2-phenylethyl)amino)(oxo)acetic Acid The desired product was prepared by substituting tert-butyl 4-bromo-1-piperidinecarboxylate and phenylethanamine for cyclohexyl bromide and benzylamine, respectively, in Example 16. MS (ESI(+)) m/z 607 (M+H)+; 1H NMR (300 MHz, DMSO-d6) δ7.99 (dd, 1H), 7.94 (dd, 1H), 7.71 (dd, 1H), 7.60–7.15 (m, 1H), 7.09 (d, 2H), 4.09–3.14 (m, 5H), 3.00–2.61 (m, 4H), 1.96–1.75 (m, 2H), 1.38 (s, 9H), 1.50–0.80 (m, 5H).

EXAMPLE 42

(benzyl(2-cyclohexyl-2-(3'-phenyl(1,1'-biphenyl)-4-yl)ethyl)amino)(oxo)acetic Acid The desired product was prepared by substituting 3-(dihydroxyboryl)-1,1'-biphenyl for 1-naphthylboronic acid in Example 16. MS (ESI(+)) m/z 518 (M+H)+; 1H NMR (300 MHz, DMSO-d6) δ7.92 (s, 1H), 7.80–7.64 (m, 6H), 7.58–7.47 (m, 3H), 7.42–7.22 (m, 7H), 7.12 (d, 1H), 4.52–4.28 (m, 1H), 3.90–3.65 (m, 2H), 2.94–2.75 (m, 2H), 1.80–1.60 (m, 3H), 1.60–1.50 (m, 5H), 1.10–1.00 (m, 3H).

EXAMPLE 43

(benzyl(2-cyclohexyl-2-(4-dibenzo(b,d)furan-2-ylphenyl)ethyl)amino)(oxo)acetic Acid The desired product was prepared by substituting dibenzo (b,d)furan-2-yl-boronic acid for 1-naphthylboronic acid in Example 16. MS (ESI(+)) m/z 532 (M+H)+; 1H NMR (300 MHz, DMSO-d6) δ7.92 (s, 1H), 7.80–7.62 (m, 5H), 7.58–7.48 (m, 3H), 7.42–7.22 (m, 6H), 7.12 (d, 1H), 4.50–4.28 (m, 1H), 3.90–3.65 (m, 2H), 2.95–2.75 (m, 2H), 1.80–1.50 (m, 8H), 1.10–1.02 (m, 3H).

EXAMPLE 44

(benzyl(2-cyclohexyl-2-(4-(8-quinolinyl)phenyl)ethyl)amino)(oxo)acetic Acid

The desired product was prepared by substituting 8-quinolinylboronic acid for 1-naphthylboronic acid in Example 16. MS (ESI(+)) m/z 493 (M+H)+; 1H NMR (300 MHz, DMSO-d6) δ8.94 (d, 1H), 8.45 (d, 1H), 8.00 (d, 1H), 7.80 (m, 1H), 7.65 (dd, 2H), 7.62–6.55 (m, 1H), 7.42–7.22 (m, 7H), 7.27 (d, 1H), 4.60–4.25 (m, 1H), 3.90–3.76 (m, 2H), 2.94–2.70 (m, 2H), 1.85–1.50 (m, 8H), 1.22–1.00 (m, 3H).

EXAMPLE 45

(benzyl(2-cyclohexyl-2-(4-(2,3-dihydro-1,4-benzodioxin-6-yl)phenyl)ethyl)amino)(oxo)acetic Acid The desired product was prepared by substituting 2,3-dihydro-1,4-benzodioxin-6-ylboronic acid for 1-naphthylboronic acid in Example 16. MS (ESI(+)) m/z 500 (M+H)+; 1H NMR (300 MHz, DMSO-d6) δ7.52 (d, 2H), 7.38–7.25 (m, 4H), 7.24–7.06 (m, 5H), 6.92 (d, 1H), 4.28 (s, 4H), 4.05–4.02 (m, 1H), 3.86–3.65 (m, 2H), 2.90–2.75 (m, 2H), 1.80–1.45 (m, 8H), 1.06–1.00 (m, 3H).

EXAMPLE 46

((2-(4-(1-naphthyl)phenyl)-2-(4-piperidinyl)ethyl)(2-phenylethyl)amino)(oxo)acetic Acid Trifluoroacetate The desired product was prepared by substituting Example 41 for Example 20E in Example 19. MS (DCI/NH3) m/z 507 (M+H)+.

EXAMPLE 47

((2-(1-acetyl-4-piperidinyl)-2-(4-(1-naphthyl)phenyl)ethyl)(2-phenylethyl)amino)(oxo)acetic Acid

EXAMPLE 47A

Ethyl ((2-(4-(1-naphthyl)phenyl)-2-(4-piperidinyl)ethyl)(2-phenylethyl)amino)(oxo)acetate The desired product was prepared by substituting Example 41 for Example 20D in Example 21A.

EXAMPLE 47B

Ethyl ((2-(1-acetyl-4-piperidinyl)-2-(4-(1-naphthyl)phenyl)ethyl)(2-phenylethyl)amino)(oxo)acetate A room temperature solution of Example 47A (50.0 mg, 0.094 mmol) in dichloromethane (2 mL) was treated with triethylamine (26.2 μL, 0.19 mmol) and acetyl chloride (10.0 μL, 0.14 mmol), stirred for 1 hour, and concentrated. The concentrate was purified by flash column chromatography on silica gel with 4:1 hexanes/ethyl acetate to provide the desired product.

EXAMPLE 47C ((2-(1-acetyl-4-piperidinyl)-2-(4-(1-naphthyl)phenyl)ethyl)(2-phenylethyl)amino)(oxo)acetic Acid The desired product was prepared by substituting Example 47B for Example 16C in Example 16D. MS (ESI(+)) m/z 549 (M+H)+; 1H NMR (300 MHz, CDCl3) δ7.91 (d, 1H), 7.86 (d, 1H), 7.77 (t, 1H), 7.56–7.01 (m, 13H), 4.77–2.57 (m, 9H), 2.16–0.77 (m, 7H), 2.10 (s, 3H).

EXAMPLE 48

((2-(1-(methylsulfonyl)-4-piperidinyl)-2-(4-(1-naphthyl)phenyl)ethyl)(2-phenylethyl)amino)(oxo)acetic Acid The desired product was prepared by substituting methanesulfonyl chloride for acetyl chloride in Example 47.

MS (ESI(+)) m/z 585 (M+H)+; 1H NMR (300 MHz, CDCl3) δ7.91 (d, 1H), 7.87 (d, 1H), 7.77 (t, 1H), 7.58–7.06 (m, 13H), 4.20–3.78 (m, 4H), 3.54–3.30 (m, 3H), 3.01–2.54 (m, 4H), 2.78 (s, 3H), 2.08–1.14 (m, 5H).

EXAMPLE 49

((2-(1-benzoyl-4-piperidinyl)-2-(4-(1-naphthyl) phenyl)ethyl)(2-phenylethyl)amino)(oxo)acetic Acid The desired product was prepared by substituting benzoyl chloride for acetyl chloride in Example 47. MS (ESI(+)) m/z 611 (M+H)+; 1H NMR (300 MHz, CDCl3)δ7.90 (d, 1H), 7.86 (d, 1H), 7.75 (t, 1H), 7.57–7.00 (m, 17H), 4.90–4.54 (m, 1H), 4.22–3.77 (m, 2H), 3.54–3.22 (m, 2H), 3.07–2.52 (m, 6H), 2.13–0.75 (m, 5H).

EXAMPLE 50

((2-(4-(1-naphthyl)phenyl)-2-(1-(phenylsulfonyl)-4-piperidinyl)ethyl)(2-phenylethyl)amino)(oxo)acetic Acid The desired product was prepared by substituting benzenesulfonyl chloride for acetyl chloride in Example 47.

MS (ESI(+)) m/z 647 (M+H)+; 1H NMR (300 MHz, CDCl3)δ7.90 (d, 1H), 7.85 (d, 1H), 7.81–7.65 (m, 2H), 7.65–6.99 (m, 17H), 4.16–3.63 (m, 3H), 3.58–3.18 (m, 2H), 2.94–2.55 (m, 3H), 2.36–2.09 (m, 2H), 2.01–1.00 (m, 6H).

EXAMPLE 51

((2-(1-(2-(diethylamino)-2-oxoethyl)-4-piperidinyl)-2-(4-(1-naphthyl)phenyl)ethyl)(2-phenylethyl) amino)(oxo)acetic Acid The desired product was prepared by substituting 2-chloro-N,N-diethylacetamide for acetyl chloride in Example 47. MS (ESI(+)) m/z 620 (M+H)+; 1H NMR (300 MHz, CDCl3) δ7.90 (dd, 1H), 7.86 (d, 1H), 7.76 (td, 1H), 7.56–7.15 (m, 13H), 7.10 (d, 2H), 4.16–3.60 (m, 4H), 3.60–3.20 (m, 6H), 3.20–2.60 (m, 4H), 2.60–1.47 (m, 8H), 1.32–1.08 (m, 6H).

EXAMPLE 52

5-((4-(2-((carboxycarbonyl)(2-phenylethyl)amino)-1-(4-(1-naphthyl)phenyl)ethyl)-1-piperidinyl) methyl)-2-furoic Acid The desired product was prepared by substituting ethyl 5-(chloromethyl)-2-furoate for acetyl chloride in Example 47. MS (DCI/NH3) m/z 631 (M+H)+.

EXAMPLE 53

((2-cyclohexyl-2-(4-(1-naphthyl)phenyl)ethyl)(2-((5-nitro-2-pyridinyl)amino)ethyl)amino)(oxo)acetic Acid The desired product was prepared by substituting N1-(6-nitro-2-pyridinyl)-1,2-ethanediamine for benzylamine in Example 16. MS (ESI(+)) m/z 567 (M+H)+; 1H NMR (300 MHz, DMSO-d6) δ8.90 (d, 1H), 8.07 (d, 1H), 7.99 (d, 1H), 7.93 (d, 1H), 7.77 (d, 1H), 7.64–7.26 (m, 8H), 6.55 (d, 1H), 6.47 (d, 1H), 4.02–3.85 (m, 1H), 3.60–3.12 (m, 4H), 3.12–2.80 (m, 2H), 1.96–0.61 (m, 11H).

EXAMPLE 54

((2-cyclohexyl-2-(4-(1-naphthyl)phenyl)ethyl)(2-(1-pyrrolidinyl)ethyl)amino)(oxo)acetic Acid The desired product was prepared by substituting 2-(1-pyrrolidinyl)ethanamine for benzylamine in Example 16.

MS (ESI(+)) m/z 499 (M+H)+; 1H NMR (300 MHz, DMSO-d6) δ8.00 (dd, 1H), 7.95 (d, 1H), 7.83 (dd, 1H), 7.61–7.28 (m, 8H), 3.95 (dd, 1H), 3.53–3.04 (m, 9H), 3.00–2.85 (m, 2H), 1.96–0.70 (m, 15H).

EXAMPLE 55

((2-cyclohexyl-2-(4-(1-naphthyl)phenyl)ethyl)(2-(1H-indol-3-yl)ethyl)amino)(oxo)acetic Acid The desired product was prepared by substituting 2-(1H-indol-3-yl)ethanamine for benzylamine in Example 16.

MS (DCI/NH3) m/z 545 (M+H)+; 1H NMR (300 MHz, DMSO-d6) δ10.80 (d, 1H), 7.97 (d, 1H), 7.92 (d, 1H), 7.67 (d, 1H), 7.60–7.24 (m, 10H), 7.08–6.90 (m, 3H), 3.99 (dd, 1H), 3.60–3.15 (m, 2H), 3.00–2.70 (m, 7H), 2.00–0.67 (m, 11H).

EXAMPLE 56

((2-cyclohexyl-2-(4-(1-naphthyl)phenyl)ethyl)(2-hydroxy-2-phenylethyl)amino)(oxo)acetic Acid The desired product was prepared by substituting 2-amino-1-phenylethanol for benzylamine in Example 16.

MS (DCI/NH3) m/z 539 (M+NH4)+; 1H NMR (300 MHz, DMSO-d6) δ8.05–7.10 (m, 16H), 4.65 (dd, 1H), 4.00–2.70 (m, 5H), 2.08–0.73 (m, 11H).

EXAMPLE 57

(((1S)-1-benzyl-2-hydroxyethyl)(2-cyclohexyl-2-(4-(1-naphthyl)phenyl)ethyl)amino)(oxo)acetic Acid The desired product was prepared by substituting (2S)-2-amino-3-phenyl-1-propanol for benzylamine in Example 16.

MS (DCI/NH3) m/z 536 (M+H)+; 1H NMR (300 MHz, DMSO-d6) δ8.04–7.89 (m, 3H), 7.86 (d, 1H), 7.66–6.98 (m, 12H), 4.37–3.76 (m, 3H), 3.60–2.70 (m, 5H), 2.03–0.60 (m, 11H).

EXAMPLE 58

(2S)-2-((carboxycarbonyl)(2-cyclohexyl-2-(4-(1-naphthyl)phenyl)ethyl)amino)-3-phenylpropanoic Acid The desired product was prepared by substituting methyl (2S)-2-amino-3-phenylpropanoate hydrochloride for benzylamine in Example 16. MS (ESI(+)) m/z 550 (M+H)+;

1H NMR (300 MHz, DMSO-d6) δ8.04–7.86 (m, 3H), 7.78 (dd, 1H), 7.68–7.01 (m, 12H), 4.60–3.71 (m, 3H), 3.69–2.90 (m, 3H), 1.94–0.50 (m, 11H).

EXAMPLE 59

(benzyl(2-(4-((1E)-3-((1,1'-biphenyl)-4-ylamino)-3-oxo-1-propenyl)phenyl)-2-cyclohexylethyl)amino) (oxo)acetic Acid The desired product was prepared by substituting (1,1'-biphenyl)-4-amine for 3,5-diphenyl-4-hydroxyaniline in Example 39. MS (ESI(+)) m/z 587 (M+H)+; 1H NMR (300 MHz, DMSO-d6) δ7.84–7.78 (m, 1H), 7.68–7.52 (m, 5H), 7.48–7.38 (m, 3H), 7.35–7.15 (m, 4H), 7.14–7.07 (m, 3H), 6.95–6.80 (m, 2H), 6.66 (dd, 1H), 6.55–6.40 (m, 1H), 3.75–3.70 (m, 2H), 2.90–2.70 (m, 2H), 2.65–2.55 (m, 1H), 1.80–1.55 (m, 2H), 1.55–1.45 (m, 6H), 1.10–0.80 (m, 3H).

EXAMPLE 60

(benzyl(2-cyclohexyl-2-(4-((1E)-3-(3,5-ditert-butylanilino)-3-oxo-1-propenyl)phenyl)ethyl)amino)(oxo)acetic Acid The desired product was prepared by substituting 3,5-ditert-butylaniline for 3,5-diphenyl-4-hydroxyaniline in Example 39. MS (ESI(+)) m/z 623 (M+H)$^+$; $^1$H NMR (300 MHz, DMSO-d$_6$) δ10.10 (s, 1H), 7.60 (d, 1H), 7.58–7.52 (m, 3H), 7.46–7.28 (m, 3H), 7.28–7.20 (m, 4H), 7.12–7.08 (m, 2H), 6.80 (dd, 1H), 4.46–4.25 (m, 1H), 3.88–3.75 (m, 1H), 2.90–2.75 (m, 2H), 2.60–2.55 (m, 1H), 1.75–1.60 (m, 3H), 1.60–1.48 (m, 5H), 1.30 (s, 18H), 1.25–1.00 (m, 3H).

EXAMPLE 61

(benzyl(2-cyclohexyl-2-(4-((1E)-3-oxo-3-(4-phenoxyanilino)-1-propenyl)phenyl)ethyl)amino)(oxo)acetic Acid The desired product was prepared by substituting 4-phenoxyaniline for 3,5-diphenyl-4-hydroxyaniline in Example 39. MS (ESI(+)) m/z 603 (M+H)$^+$; $^1$H NMR (300 MHz, DMSO-d$_6$) δ7.73 (d, 1H), 7.60–7.50 (m, 3H), 7.42–7.28 (m, 6H), 7.27–7.10 (m, 4H), 7.10–6.95 (m, 3H), 6.80–6.68 (m, 2H), 6.62 (dd, 1H), 4.5–3.72 (m, 2H), 2.90–2.80 (m, 2H), 2.80–2.70 (m, 1H),1.70–1.58 (m, 3H), 1.58–1.44 (m, 5H), 1.05–0.96 (m, 3H).

EXAMPLE 62

(benzyl(2-cyclohexyl-2-(4-((1E)-3-(4-(2,3-dimethylphenyl)-1-piperazinyl)-3-oxo-1-propenyl)phenyl)ethyl)amino)(oxo)acetic Acid The desired product was prepared by substituting 1-(2,3-dimethylphenyl)piperazine for 3,5-diphenyl-4-hydroxyaniline in Example 39. MS (ESI(+)) m/z 608 (M+H)$^+$;

$^1$H NMR (300 MHz, DMSO-d$_6$) δ7.68 (dd, 2H), 7.56–7.25 (m, 5H), 7.52 (d, 1H), 7.25–7.18 (m, 3H), 7.12–7.02 (m, 2H), 6.90 (d, 1H), 3.90–3.82 (m, 2H), 3.80–3.70 (m, 2H), 3.60–3.40 (m, 4H), 2.80 (br s, 3H), 2.55 (m, 1H), 2.22 (d, 3H), 1.80–1.60 (m, 3H), 1.60–1.48 (m, 3H), 1.40–1.00 (m, 5H).

EXAMPLE 63

((2-(4-((1E)-3-(4-benzhydryl-1-piperazinyl)-3-oxo-1-propenyl)phenyl)-2-cyclohexylethyl)(benzyl)amino)(oxo)acetic Acid The desired product was prepared by substituting 1-benzhydrylpiperazine for 3,5-diphenyl-4-hydroxyaniline in Example 39. MS (ESI(+)) m/z 670 (M+H)$^+$; $^1$H NMR (300 MHz, DMSO-d$_6$) δ7.90–7.75 (m, 2H), 7.62 (dd, 2H), 7.50–7.40 (m, 4H), 7.38–7.25 (m, 6H), 7.22–7.16 (m, 6H), 7.10 (dd, 1H), 4.45–4.20 (m, 1H), 3.85–3.66 (m, 2H), 2.90–2.70 (m, 1H), 2.48–2.25 (m, 2H), 1.65–1.56 (m, 2H), 1.55–1.45 (m, 5H), 1.35–0.96 (m, 4H).

EXAMPLE 64 oxo((2-phenylethyl)((4,1'-binaphth-1-yl)methyl)amino)acetic Acid

The desired product was prepared by substituting 4-hydroxy-1-naphthaldehyde and phenylethanamine for 2,3-dichloro-4-hydroxybenzaldehyde and benzylamine, respectively, in Example 5. MS (ESI(+)) m/z 460 (M+H)$^+$;

$^1$H NMR (300 MHz, CDCl$_3$) δ7.90–7.70 (m, 5H), 7.60–6.6 (m, 13H), 5.70–5.00 (m, 2H), 4.10–3.90 (m, 2H), 2.95–2.75 (m, 2H).

EXAMPLE 65

(((4-((1,3-benzothiazol-2-ylsulfanyl)methyl)phenyl)(cyclohexyl)methoxy)amino)-(oxo)acetic Acid

EXAMPLE 65A

O-((4-((1,3-benzothiazol-2-ylsulfanyl)methyl)phenyl}(cyclohexyl)methyl)hydroxylamine The desired product was prepared by substituting 4-((1,3-benzothiazol-2-ylsulfanyl)methyl)benzaldehyde for 4-(2-quinolinyl)benzaldehyde in the procedure described in *Tetrahedron: Asymmetry* 1996, 7, 2645.

EXAMPLE 65B (((4-((1,3-benzothiazol-2-ylsulfanyl)methyl)phenyl)-(cyclohexyl)methoxy)amino)-(oxo)acetic Acid The desired product was prepared by substituting Example 65A for 2-(4-((amino)oxy)(cyclohexyl)methyl)-phenyl)quinoline in Example 4. MS (ESI(-) m/z 455 (M–H)$^-$;

$^1$H NMR (500 MHz, DMSO-d$_6$) δ8.01 (d, 2H), 7.89 (d, 2H), 7.47 (m, 3H), 7.37 (t, 1H), 7.27 (d, 2H), 4.66 (s, 2H), 4.65 (d, 1H), 1.97 (m, 1H), 1.67 (m, 2H), 1.57 (m, 2H), 1.25 (m, 1H), 1.15–1.02 (m, 4H), 0.88 (m, 1H).

EXAMPLE 66

((cyclohexyl(4-(2,3-dihydro-1,4-benzodioxin-6-yl)phenyl)methoxy)amino)(oxo)acetic Acid

EXAMPLE 66A 6-(4-((amino)oxy)(cyclohexyl)methyl)phenyl)-2,3-dihydro-1,4-benzodioxine The desired product was prepared by substituting Example 3A and 2,3-dihydro-1,4-benzodioxin-6-ylboronic acid for Example 1A and 1-naphthylboronic acid, respectively, in Example 16A.

EXAMPLE 66B ((cyclohexyl(4-(2,3-dihydro-1,4-benzodioxin-6-yl)phenyl)methoxy)amino)(oxo)acetic Acid The desired product was prepared by substituting Example 66A for 2-(4-((amino)oxy)(cyclohexyl)methyl)phenyl)-quinoline in Example 4. MS (ESI(-)) m/z 410 (M–H)$^-$;

$^1$H NMR (500 MHz, DMSO-d$_6$) δ11.65 (br s, 1H), 7.55 (d, 2H), 7.32 (d, 2H), 7.15 (m, 2H), 6.92 (d, 1H), 4.68 (d, 1H), 4.27 (s, 4H), 2.00 (m, 1H), 1.69 (m, 2H), 1.58 (m, 2H), 1.32 (m, 1H), 1.2–1.1 (m, 4H), 0.90 (m, 1H).

EXAMPLE 67

(((4-(decyloxy)-1-naphthyl)methyl)(2-phenylethyl)amino)-(oxo)acetic Acid

EXAMPLE 67A 4-(decyloxy)-1-naphthaldehyde

The desired product was prepared by substituting 4-hydroxy-1-naphthaldehyde and 1-chlorodecane for Example 20C and tert-butyl bromoacetate, respectively, in Example 20D.

EXAMPLE 67B (((4-(decyloxy)-1-naphthyl)methyl)(2-phenylethyl)amino)-(oxo)acetic Acid The desired product was prepared by substituting Example 67A and phenylethanamine for Example 5B and benzylamine, respectively, in Examples 5C–5E. MS (ESI (+)) m/z 490 (M+H)$^+$; $^1$H NMR (300 MHz, CDCl$_3$) δ8.35 (d, 1H), 7.84 (d, 1H), 7.60–7.48 (m, 2H), 7.30–7.15 (m, 4H), 7.15–7.05 (m, 2H), 6.77 (t, 1H), 5.07–5.04 (m, 1H), 4.18–4.08 (m, 2H), 3.93–3.88 (m, 2H), 3.52–3.12 (m, 1H), 2.85–2.70 (m, 2H), 2.00–1.90 (m, 2H), 1.60–1.50 (m, 4H), 1.48–1.20 (m, 10H), 0.92–0.80 (t, 3H).

EXAMPLE 68

(((4-(octadecyloxy)-1-naphthyl)methyl)(2-phenylethyl)amino)-(oxo)acetic Acid

The desired product was prepared by substituting 1-chlorooctadecane for 1-chlorodecane in Example 67. MS (ESI(+)) m/z 602 (M+H)$^+$; $^1$H NMR (300 MHz, CDCl$_3$) δ8.48–8.34 (m, 1H), 7.86–7.82 (m, 1H), 7.58–7.48 (m, 2H), 7.28–7.20 (m, 4H), 7.08–7.04 (m, 2H), 6.76 (t, 1H), 5.07–5.05 (m, 1H), 4.18–4.10 (m, 2H), 3.92–3.86 (m, 2H), 3.60–3.45 (m, 1H), 2.80–2.70 (m, 2H), 1.98–1.86 (m, 2H), 1.62–1.50 (m, 2H), 1.40–1.15 (m, 30H), 0.88 (t, 3H).

EXAMPLE 69

((2-(1,1'-biphenyl)-3-yl-2-cyclohexylethyl)(2-phenylethyl)amino)(oxo)acetic Acid

EXAMPLE 69A (3-bromophenyl)(cyclohexyl)acetonitrile

The desired product was prepared by substituting 3-bromophenylacetonitrile for 4-bromophenylacetonitrile in Example 1A.

EXAMPLE 69B ((2-(1,1'-biphenyl)-3-yl-2-cyclohexylethyl)(2-phenylethyl)amino)(oxo)acetic Acid The desired product was prepared by substituting Example 69A, phenylboronic acid, and phenylethanamine for Example 1A, 1-naphthylboronic acid, and benzylamine, respectively, in Example 16. $^1$H NMR (300 MHz, CDCl$_3$) δ7.60–7.53 (m, 2H), 7.46–7.42 (m, 3H), 7.38–7.31 (m, 3H), 7.27–7.19 (m, 2H), 7.11–7.01 (m, 4H), 4.27–3.88 (m, 2H), 3.57–3.31 (m, 2H), 2.90–2.62 (m, 3H), 1.95–1.42 (m, 6H), 1.28–0.78 (m, 5H).

EXAMPLE 70

(((4-butoxy-1-naphthyl)methyl)(2-phenylethyl)amino)-(oxo)acetic Acid

The desired product was prepared by substituting 1-bromobutane for 1-chlorodecane in Example 67. MS (ESI(+)) m/z 406 (M+H)$^+$; $^1$H NMR (300 MHz, CDCl$_3$) δ8.36 (d, 1H), 7.84 (d, 1H), 7.47–7.30 m, 2H), 7.20–7.18 (m, 4H), 7.10–7.02 (m, 2H), 6.86 (t, 1H), 5.08–5.02 (m, 1H), 4.20–4.10 (m, 2H), 3.90–3.84 (m, 2H), 3.54–3.10 (m, 1H), 2.80–2.70 (m, 2H), 2.10–1.86 (m, 2H), 1.68–1.56 (m, 2H), 1.04 (t, 3H).

EXAMPLE 71 oxo((2-phenylethyl)((4-(tetradecyloxy)-1-naphthyl)methyl)amino)acetic Acid

The desired product was prepared by substituting 1-bromotetradecane for 1-chlorodecane in Example 67. MS (ESI(+)) m/z 546 (M+H)$^+$; $^1$H NMR (300 MHz, CDCl$_3$) δ8.32 (d, 1H), 7.84 (d, 1H), 7.55–7.30 (m, 2H), 7.20–7.18 (m, 4H), 7.10–7.02 (m, 2H), 6.90 (t, 1H), 5.05–4.70 (m, 1H), 4.15–3.85 (m, 2H), 3.70–3.50 (m, 2H), 3.30–3.10 (m, 1H), 2.80–2.65 (m, 2H), 2.10–1.86 (m, 3H), 1.40–1.15 (m, 6H), 0.98 (t, 3H).

EXAMPLE 72

((2-cyclohexyl-2-(3-(1-naphthyl)phenyl)ethyl)(2-phenylethyl)amino)(oxo)acetic Acid The desired product was prepared by substituting 1-naphthylboronic acid for phenylboronic acid in Example 69.

MS (APCI(-)) m/z 504 (M-H)$^-$; $^1$H NMR (300 MHz, CDCl$_3$) δ7.88 (dd, 2H), 7.78–7.74 (m, 1H), 7.53–7.06 (m, 13H), 4.15–4.01 (m, 2H), 3.51–3.33 (m, 2H), 2.84–2.72 (m, 3H), 1.96–1.44 (m, 6H), 1.28–0.82 (m, 5H).

EXAMPLE 73

((2-cyclohexyl-2-(3-(2-naphthyl)phenyl)ethyl)(2-phenylethyl)amino)(oxo)acetic Acid The desired product was prepared by substituting 2-naphthylboronic acid for phenylboronic acid in Example 69.

MS (APCI(-)) m/z 504 (M-H)$^-$; $^1$H NMR (300 MHz, CDCl$_3$) δ7.99 (br s, 1H), 7.93–7.84 (m, 3H), 7.70 (dd, 1H), 7.58–7.36 (m, 5H), 7.29–7.16 (m, 3H), 7.11–7.04 (m, 3H), 4.27–3.87 (m, 2H), 3.58–3.32 (m, 2H), 2.94–2.65 (m, 3H), 1.98–1.43 (m, 6H), 1.23–0.80 (m, 5H).

EXAMPLE 74

((2-cyclohexyl-2-(3'-phenyl(1,1'-biphenyl)-3-yl)ethyl)(2-phenylethyl)amino)(oxo)acetic Acid The desired product was prepared by substituting 3-(dihydroxyboryl)-1,1'-biphenyl for phenylboronic acid in Example 69. MS (APCI(-)) m/z 530 (M-H)$^-$; $^1$H NMR (300 MHz, CDCl$_3$) δ7.77–7.75 (m, 1H), 7.68–7.64 (m, 2H), 7.60–7.55 (m, 1H), 7.53–7.44 (m, 5H), 7.40–7.32 (m, 3H), 7.29–7.15 (m, 3H), 7.11–7.03 (m, 3H), 4.30–3.87 (m, 2H), 3.59–3.32 (m, 2H), 2.92–2.65 (m, 3H), 1.95–1.43 (m, 6H), 1.23–0.78 (m, 5H).

It will be evident to one skilled in the art that the invention is not limited to the forgoing examples, and that it can be embodied in other specific forms without departing from the essential attributes thereof. Thus, it is desired that the examples be considered as illustrative and not restrictive, reference being made to the claims, and that all changes which come within the meaning and range of equivalency of the claims be embraced therein.

What is claimed is:

1. A compound of formula (I)

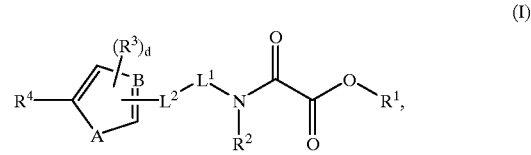

or therapeutically acceptable salts thereof, wherein
A is C(H)=C(H);
B is C(H);
d is 0, 1, or 2;
$L^1$ is a covalent bond or O;
$L^2$ is a member selected from the group consisting of $CH(R^6)$ and $CH_2CH(R^6)$;
$R^1$ is a member selected from the group consisting of hydrogen and a carboxy protecting group;
$R^2$ is a member selected from the group consisting of hydrogen, aminoalkyl, loweralkyl, cycloalkyl, cycloalkylalkyl, cycloalkenyl, cycloalkenylalkyl, aryl, arylalkyl, hydroxyalkyl, and haloalkyl;
each $R^3$ is independently a member selected from the group consisting of hydrogen, loweralkoxy, alkoxyalkyl, alkoxyalkenyl, alkoxyalkoxy, alkoxycarbonyl, alkoxycarbonylalkyl, alkoxycarbonylalkenyl, alkoxycarbonylalkoxy, aryl, arylalkyl, arylalkenyl, arylalkoxy, carboxamido, carboxamidoalkyl, carboxamidoalkenyl, carboxamidoalkoxy, carboxy, carboxyalkyl, carboxyalkenyl, carboxyalkoxy, and halo; or
two of $R^3$ are on adjacent atoms and, taken together with the atoms to which they are attached, are phenyl, wherein the phenyl can be optionally substituted with one or two substituents independently are a member selected from the group consisting of loweralkoxy, alkoxycarbonylalkenyl, alkoxycarbonylalkoxy, aryl, carboxamidoalkenyl, carboxamidoalkoxy, carboxyalkenyl, carboxyalkoxy, and halo;
$R^4$ is a member selected from the group consisting of alkoxycarbonylalkyl, alkoxycarbonylalkenyl, aryl, arylalkyl, arylalkoxy, arylthioxyalkyl, carboxamidoalkenyl, carboxamidoalkyl, carboxyalkyl, carboxylalkenyl, and $R^7$-T-;
$R^6$ is a member selected from the group consisting of hydrogen, aryl, arylalkyl, cycloalkyl, cycloalkylalkyl, cycloalkenyl, and cycloalkenylalkyl;
$R^7$ is aryl; and, T is a member selected from the group consisting of $C(O)N(R^8)$, $N(R^8)C(O)$, $N(R^8)$, $OC(O)N(R^8)$, $N(R^8)C(O)O$, $C(O)$, $OC(O)$, $(O)CO$, O, S, $S(O)$, $SO_2$, $C(O)$, $OC(O)O$, $N(R^8)C(O)N(R^8)$, and $C(O)OC(O)$;
wherein the asymmetric groups defining T are drawn with their left ends attached to $R^7$ and their right ends attached to the ring and; and
$R^8$ is a member selected from the group consisting of hydrogen and alkyl.

2. A compound according to claim 1 of formula (III)

(III)

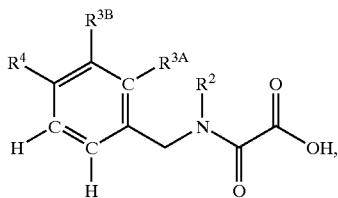

or therapeutically acceptable salts thereof, wherein
$R^2$ and $R^4$ are as defined in claim 1;
$R^{3A}$ is a member selected from the group consisting of hydrogen, loweralkoxy, alkoxycarbonylalkenyl, alkoxycarbonylalkoxy, aryl, carboxamidoalkenyl, carboxamidoalkoxy, carboxyalkenyl, carboxyalkoxy, and halo; and
$R^{3B}$ is a member selected from the group consisting of hydrogen and halo.

3. A compound according to claim 2 wherein $R^2$ is a member selected from the group consisting of hydrogen, arylalkyl, and cycloalkyl.

4. A compound according to claim 2 wherein $R^4$ is aryl.

5. A compound according to claim 1 of formula (IV)

(IV)

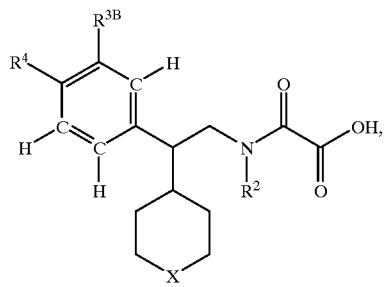

or therapeutically acceptable salts thereof, wherein
$R^2$ and $R^4$ are as defined in claim 1;
$R^{3b}$ is a member selected from the group consisting of hydrogen and aryl; and
X is $CH_2$.

6. A compound according to claim 5 wherein $R^2$ is a member selected from the group consisting of hydrogen, arylalkyl, arylalkyl, and aminoalkyl.

7. A compound according to claim 5 wherein $R^4$ is a member selected from the group consisting of, aryl, alkoxycarbonylalkenyl, carboxyalkenyl, and carboxamidoalkenyl.

8. A compound according to claim 1 of formula (V)

(V)

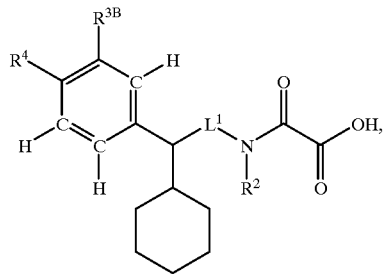

or therapeutically acceptable salts thereof, wherein
$L^1$, $R^2$, and $R^4$ are as defined in claim 1; and
$R^{3b}$ is hydrogen.

9. A compound according to claim 8 wherein $L^1$ is a covelent bond.

10. A compound according to claim 8 wherein $L^1$ is O.

11. A compound according to claim 8 wherein $R^2$ is hydrogen.

12. A compound according to claim 8 wherein $R^4$ is aryl.

13. A compound according to claim 1 of formula (VI)

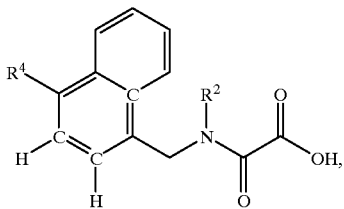

(VI)

or therapeutically acceptable salts thereof, wherein $R^2$ and $R^4$ are as defined in claim 1.

14. A compound according to claim 13 wherein $R^2$ is a member selected from the group consisting of hydroxyalkyl and arylalkyl.

15. A compound according to claim 13 wherein $R^4$ is aryl.

16. A method for preparing a compound of formula (I), the method comprising:
(a) reacting a compound of formula (Ia)

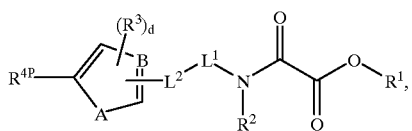

(Ia)

or therapeutically acceptable salts thereof,
wherein A, B, d, $L^1$, $L^2$, $R^1$, and $R^2$ are as defined in claim 1; and
$R^{4P}$ is a member selected from the group consisting of chloride, bromide, iodide, hydroxy, and trifluoromethanesulfonate
with a coupling partner selected from the group consisting of a substituted alkene, an optionally substituted arylboronic acid, an optionally substituted aryl trialkylstannane, and an optionally substituted alkyl halide,
a base, and, optionally, a palladium catalyst; and
(b) optionally hydrolyzing the product of step (a).

17. The method of claim 16 wherein the palladium catalyst is a member selected from the group consisting of tetrakistriphenylphosphinepalladium(0), Pd(II) bis(triphenylphosphine)dichloride, and dipalladium tris (dibenzylidineacetone).

18. A method for inhibiting protein tyrosine phosphatase comprising administering a therapeutically effective amount of a compound of claim 1.

19. A method of treating a disease selected from the group consisting of type II diabetes and obesity comprising administering to a patient a therapeutically effective amount of the compound of claim 1.

20. A composition comprising a compound of claim 1 and a therapeutically suitable excipient.

21. A compound selected from the group consisting of
((2-(4-bromophenyl)-2-cyclohexylethyl)amino)(oxo) acetic acid,
(benzyl(2-(4-bromophenyl)-2-cyclohexylethyl)amino) (oxo)acetic acid,
(((4-bromophenyl)(cyclohexyl)methoxy)amino)(oxo) acetic acid,
(benzyl(2,3-dichloro-4-(1-naphthyl)benzyl)amino) (oxo) acetic acid,
N-benzyl-2-hydroxy-N-((4,1'-binaphth-1-yl)methyl) amino)(oxo)acetic acid,
(benzyl(2-chloro-4-(1-naphthyl)benzyl)amino)(oxo) acetic acid,
(benzyl(2-methoxy-4-(1-naphthyl)benzyl)amino)(oxo) acetic acid,
((2-hydroxyethyl)((4,1'-binaphth-1-yl)methyl)amino) (oxo)acetic acid,
(benzyl(2-cyclohexyl-2-(4-(1-naphthyl)phenyl)ethyl) amino)(oxo)acetic acid,
((2-cyclohexyl-2-(4-(1-naphthyl)phenyl)ethyl)(2-phenylethyl)amino)(oxo)acetic acid,
((2-cyclohexyl-2-(4-(1-naphthyl)phenyl)ethyl)(2-(3,4-dimethoxyphenyl)ethyl)amino)(oxo)acetic acid,
(benzyl(2-(carboxymethoxy)-4-(1-naphthyl)benzyl) amino)-(oxo)acetic acid,
(benzyl(2-(2-tert-butoxy-2-oxoethoxy)-4-(1-naphthyl)-benzyl)amino)(oxo)acetic acid,
3-(((2-((benzyl(carboxycarbonyl)amino)methyl)-5-(1-naphthyl)phenoxy)acetyl)amino)benzoic acid,
(benzyl(2-(2-(((4-(methoxycarbonyl)cyclohexyl)methyl)-amino)-2-oxoethoxy)-4-(1-naphthyl)benzyl)amino) (oxo)acetic acid,
((2-methoxy-4-(1-naphthyl)benzyl)(2-phenylethyl) amino)(oxo)acetic acid,
((2,3-dichloro-4-(1-naphthyl)benzyl)(2-phenylethyl) amino)(oxo)acetic acid,
((2-(4-(((carboxycarbonyl)amino)sulfonyl)phenyl)ethyl) (2-cyclohexyl-2-(4-(1-naphthyl)phenyl)ethyl)amino)- (oxo)acetic acid,
(benzyl((5-(1-naphthyl)(1,1'-biphenyl)-2-yl)methyl) amino)(oxo)acetic acid,
(benzyl((4'-formyl-5-(1-naphthyl)(1,1'-biphenyl)-2-yl) methyl)amino)(oxo)acetic acid,
(benzyl(2-((1E)-3-tert-butoxy-3-oxo-1-propenyl)-4-(1-naphthyl)benzyl)amino)(oxo)acetic acid,
(2E)-3-(2-((benzyl(carboxycarbonyl)amino)methyl)-5-(1-naphthyl)phenyl)-2-propenoic acid,
(benzyl(2-(4-((1E)-3-tert-butoxy-3-oxo-1-propenyl) phenyl)-2-cyclohexylethyl)amino)(oxo)acetic acid,
(((1,1'-biphenyl)-4-yl(cyclohexyl)methoxy)amino)(oxo) acetic acid,
(2E)-3-(4-(2-(benzyl(carboxycarbonyl)amino)-1-cyclohexyl-ethyl)phenyl)-2-propenoic acid,
(benzyl(2-cyclohexyl-2-(4-((1E)-3-(4-hydroxy-3,5-diphenyl-anilino)-3-oxo-1-propenyl)phenyl)ethyl) amino)-(oxo)acetic acid,
(benzyl(2-cyclohexyl-2-(4-(3-(4-hydroxy-3,5-diphenyl-anilino)-3-oxopropyl)phenyl}ethyl)amino)(oxo)acetic acid,
(benzyl(2-cyclohexyl-2-(3'-phenyl(1,1'-biphenyl)-4-yl)- ethyl)amino)(oxo)acetic acid,
((2-cyclohexyl-2-(4-(1-naphthyl)phenyl)ethyl)(2-hydroxy-2-phenylethyl)amino)(oxo)acetic acid,
(((1S)-1-benzyl-2-hydroxyethyl)(2-cyclohexyl-2-(4-(1-naphthyl)phenyl)ethyl)amino)-(oxo)acetic acid,
(2S)-2-((carboxycarbonyl)(2-cyclohexyl-2-(4-(1-naphthyl)-phenyl)ethyl)amino)-3-phenylpropanoic acid,
(benzyl(2-(4-((1E)-3-((1,1'-biphenyl)-4-ylamino)-3-oxo-1-propenyl)phenyl)-2-cyclohexylethyl)amino)(oxo) acetic acid, (benzyl(2-cyclohexyl-2-(4-((1E)-3-(3,5-ditert-butyl-anilino)-3-oxo-1-propenyl)phenyl)ethyl)amino)-(oxo)acetic acid, (benzyl(2-cyclohexyl-2-(4-((1E)-3-oxo-3-(4-phenoxy-anilino)-1-propenyl)phenyl)ethyl)amino)(oxo)acetic acid, (((4-(decyloxy)-1-naphthyl)methyl)(2-phenylethyl)-amino)(oxo)acetic acid, (((4-(octadecyloxy)-1-naphthyl)methyl)(2-phenylethyl)-amino)(oxo)acetic acid, ((2-(1,1'-biphenyl)-3-yl-2-cyclohexylethyl)(2-phenyl-ethyl)amino)(oxo)acetic acid, (((4-butoxy-1-naphthyl)methyl)(2-phenylethyl)amino)(oxo)acetic acid, oxo((2-phenylethyl)((4-(tetradecyloxy)-1-naphthyl)-methyl)amino)acetic acid, ((2-cyclohexyl-2-(3-(1-naphthyl)phenyl)ethyl)(2-phenylethyl)amino)(oxo)acetic acid, ((2-cyclohexyl-2-(3-(2-naphthyl)phenyl)ethyl)(2-phenylethyl)amino)(oxo)acetic acid, and ((2-cyclohexyl-2-(3'-phenyl(1,1'-biphenyl)-3-yl)-ethyl)(2-phenylethyl)amino)(oxo)acetic acid.

22. The compound (benzyl(2-cyclohexyl-2-(4-(1-naphthyl)phenyl)ethyl)amino)(oxo)acetic acid, or a therapeutically acceptable salt thereof.

23. A method of treating a disease selected from the group consisting of type II diabetes and obesity comprising administering to a patient a therapeutically effective amount of the compound (benzyl(2-cyclohexyl-2-(4-(1-naphthyl)phenyl)ethyl)amino)(oxo)acetic acid, or a therapeutically acceptable salt thereof.

24. A composition comprising the compound (benzyl(2-cyclohexyl-2-(4-(1-naphthyl)phenyl)ethyl)amino)(oxo)acetic acid, or a therapeutically acceptable salt thereof, and a therapeutically acceptable excipient.

* * * * *